US009949659B2

(12) United States Patent
Armoundas

(10) Patent No.: US 9,949,659 B2
(45) Date of Patent: Apr. 24, 2018

(54) SYSTEM AND METHOD FOR DETERMINING DYNAMIC ELECARDIOGRAPHIC ISCHEMIC CHANGES

(71) Applicant: The General Hospital Corporation, Boston, MA (US)

(72) Inventor: Antonis Armoundas, Lincoln, MA (US)

(73) Assignee: The General Hospital Corporation, Boston, MA (US)

( * ) Notice: Subject to any disclaimer, the term of this patent is extended or adjusted under 35 U.S.C. 154(b) by 294 days.

(21) Appl. No.: 14/671,395

(22) Filed: Mar. 27, 2015

(65) Prior Publication Data
US 2015/0272464 A1 Oct. 1, 2015

Related U.S. Application Data

(60) Provisional application No. 61/971,361, filed on Mar. 27, 2014, provisional application No. 62/015,578, filed on Jun. 23, 2014.

(51) Int. Cl.
| | |
|---|---|
| *A61B 5/0472* | (2006.01) |
| *A61B 5/0464* | (2006.01) |
| *A61B 5/0456* | (2006.01) |
| *A61B 5/042* | (2006.01) |
| *A61B 5/0452* | (2006.01) |
| *A61B 5/026* | (2006.01) |
| *A61B 5/00* | (2006.01) |
| *A61B 5/0408* | (2006.01) |
| *A61M 5/172* | (2006.01) |
| *A61N 1/365* | (2006.01) |

(52) U.S. Cl.
CPC .......... *A61B 5/0464* (2013.01); *A61B 5/0006* (2013.01); *A61B 5/026* (2013.01); *A61B 5/042* (2013.01); *A61B 5/0456* (2013.01); *A61B 5/04085* (2013.01); *A61B 5/04525* (2013.01); *A61M 5/1723* (2013.01); *A61M 2230/04* (2013.01); *A61N 1/36592* (2013.01)

(58) Field of Classification Search
CPC ............................ A61B 5/0472; A61B 4/0464
USPC ................................... 600/508, 516
See application file for complete search history.

(56) References Cited

U.S. PATENT DOCUMENTS

| 5,113,869 | A * | 5/1992 | Nappholz | ............ | A61B 5/0006 |
| | | | | | 128/903 |
| 2008/0194978 | A1 * | 8/2008 | Beker | .................. | A61B 5/0472 |
| | | | | | 600/516 |

* cited by examiner

*Primary Examiner* — Carl H Layno
*Assistant Examiner* — Jon Eric C Morales
(74) *Attorney, Agent, or Firm* — Quarles & Brady LLP

(57) ABSTRACT

A system and method for determining and controlling a cardiac condition of a subject are provided. In some aspects, the method includes acquiring ECG signals using one or more electrodes configured to sense a cardiac activity of a subject, and analyzing the ECG signals to delineate cardiac waveforms on a beat-to-beat basis. The method also includes identifying, in the delineated cardiac waveforms, characteristic points associated with different phases of cardiac activity, and for each delineated cardiac waveform, computing an ischemic index using the ECG signals corresponding to a ventricular depolarization period and a ventricular repolarization period, wherein the ventricular depolarization period and the ventricular repolarization period are defined by the identified characteristic points. The method further includes determining a cardiac condition of the subject using each computed ischemic index.

27 Claims, 19 Drawing Sheets

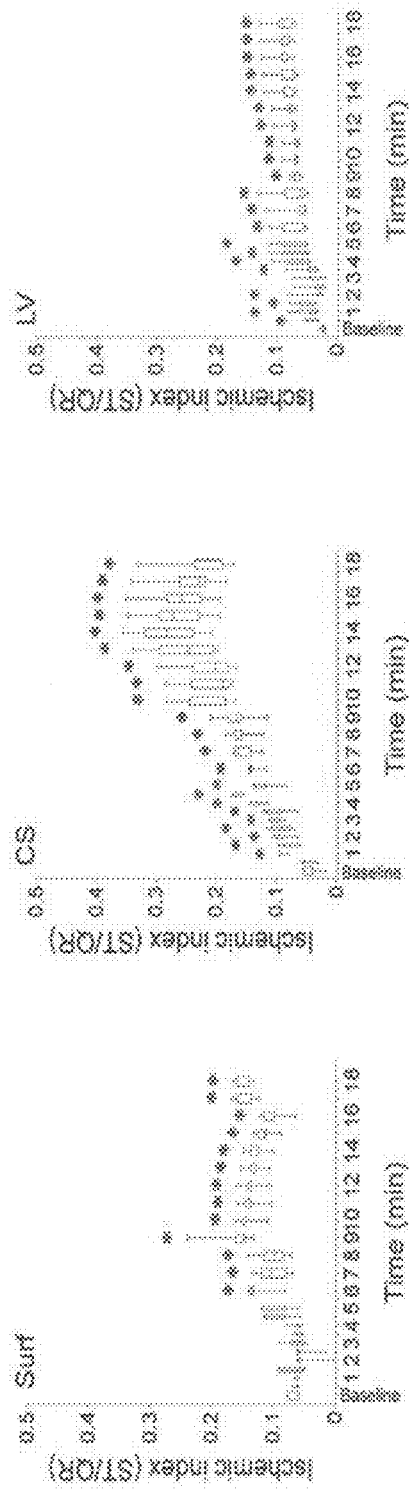
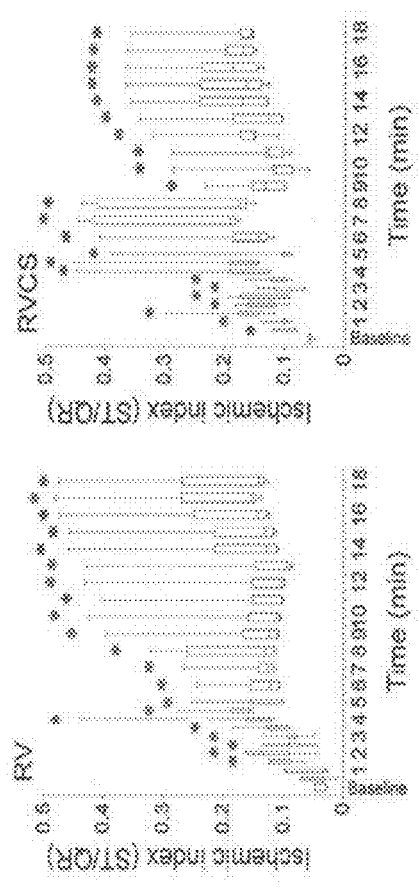
FIG. 5A  FIG. 5B  FIG. 5C  FIG. 5D  FIG. 5E

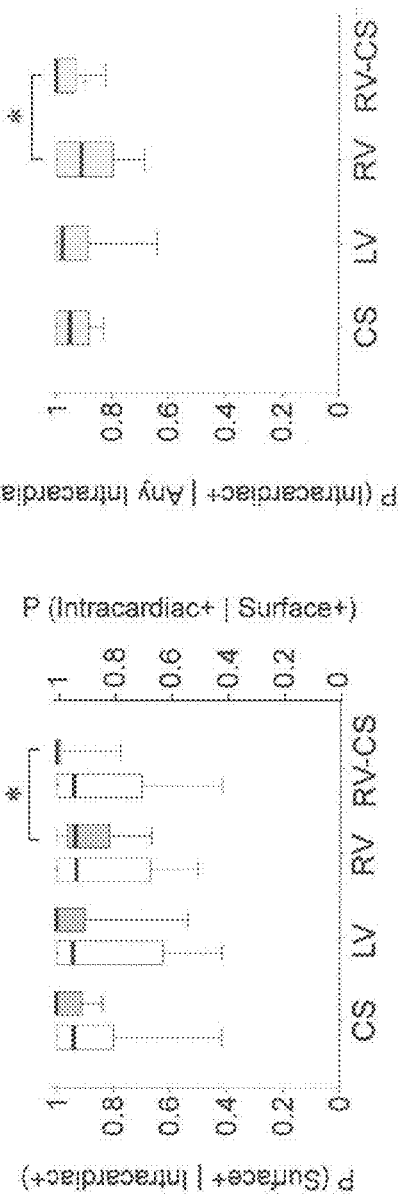
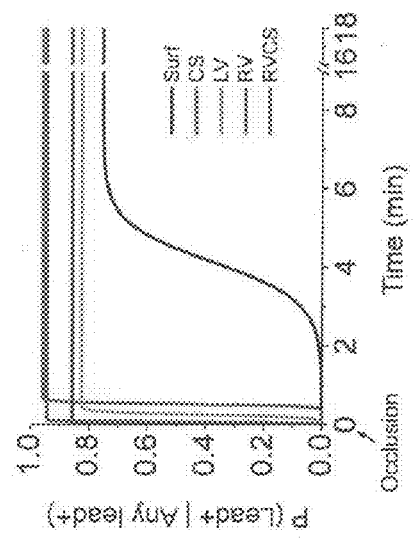
FIG. 6A  FIG. 6B  FIG. 6C

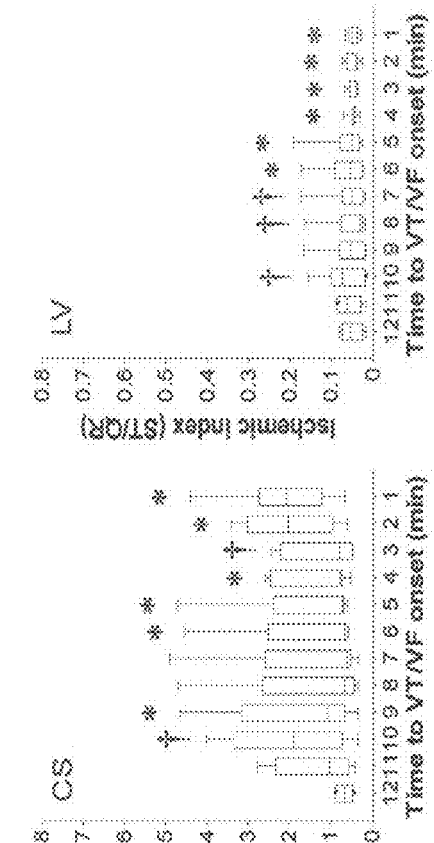
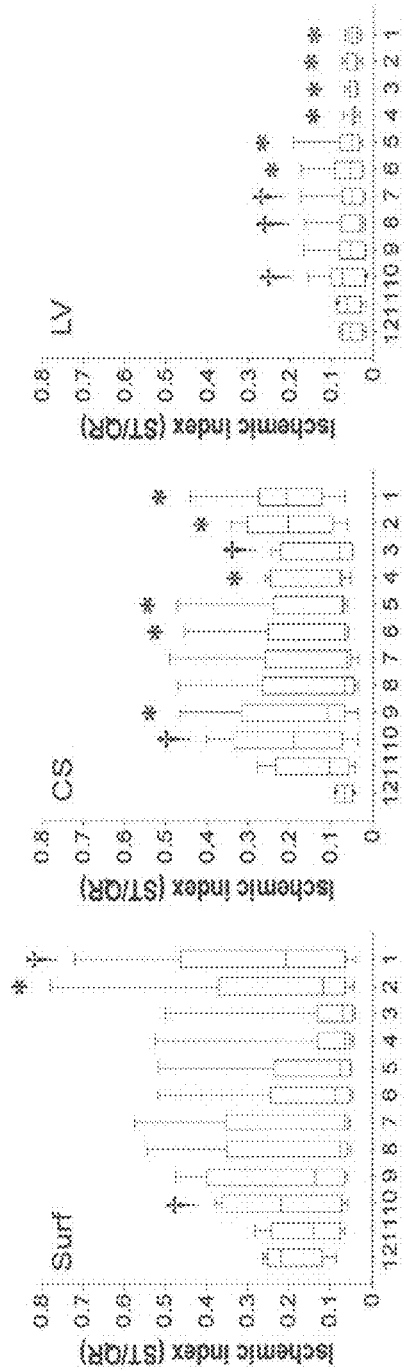
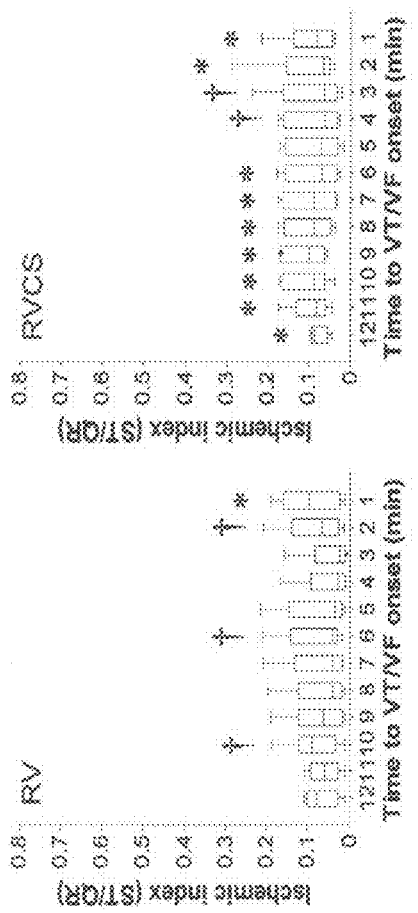

SYSTEM AND METHOD FOR DETERMINING DYNAMIC ELECARDIOGRAPHIC ISCHEMIC CHANGES

CROSS-REFERENCE TO RELATED APPLICATIONS

This application claims the benefit of U.S. Provisional Patent Application Ser. No. 61/971,361 filed on Mar. 27, 2014, and entitled "SYSTEMS AND METHODS TO CAPTURE THE ONSET OF DYNAMIC ELECTROCARDIOGRAPHIC ISCHEMIC CHANGES" and U.S. Provisional Patent Application Ser. No. 62/015,578 filed on Jun. 23, 2014, and entitled "SYSTEMS AND METHODS TO CAPTURE THE ONSET OF DYNAMIC ELECTROCARDIOGRAPHIC ISCHEMIC CHANGES."

STATEMENT REGARDING FEDERALLY SPONSORED RESEARCH

This invention was made with government support under 1R21AG035128 awarded by the National Institutes of Health. The government has certain rights in the invention.

BACKGROUND

The present disclosure relates to subject monitoring. More particularly, the present disclosure is directed to determining and/or controlling a condition of a subject using measures of cardiac activity.

Myocardial ischemia ("MI") refers to the condition when blood flow to the heart muscle is substantially decreased due to partial or complete blockage of coronary arteries. This reduces oxygen supply to the heart, resulting in heart muscle damage that in turn reduces the ability to pump blood efficiently. If ischemia is severe or prolonged, it may lead to more severe consequences, such as fatal tachy-arrhythmic events. Therefore, early diagnosis and risk stratification of patients with acute or long-term MI is essential to guide prompt interventions necessary to obtaining optimal clinical outcomes.

Presently, electrocardiographic ST-segment monitoring using body surface leads is widely used to detect acute MI. Specifically, the ST-segment is a flat, isolectric section of the electrocardiogram ("ECG") signal, representing the interval between ventricular depolarization and repolarization found between the end of the S-wave, or the J-point, and the beginning of the T-wave. In the standard 12-lead configuration, ST-segment deviation is the most commonly used determinant of ongoing ischemia, and a strong predictor of the associated mortality. However, the sensitivity in detecting acute MI using this previous approach remains inadequately low. Whether due to the variability of the ischemia-induced changes in various ECG leads, as evidenced by body surface potential mapping, or the inaccuracy in detecting elevated J-points, body surface ECGs may not reveal sub-endocardial, and even severe transmural ischemia.

With the advent of implantable cardioverter defibrillators ("ICD"), defibrillation of ventricular tachy-arrhythmias has resulted in significant improvements in survival. Recent evidence also suggested that continuous monitoring of a patient's ST-segment changes in intra-cardiac electrograms may allow an implanted device to detect acute closure of a coronary artery, which could lead to a reduction in symptom-to-door time and thereby potentially improved clinical outcomes. In addition, it has been recently shown that the high-risk period for sudden death of patients who survive an acute MI extends beyond the hospitalization period, mostly due to recurrent MI or extension of the infarcted area. These results imply that early detection of MI, either in the ambulatory ECG, or from an implantable device, can provide significant therapeutic potential for high-risk patients.

Hence, in light of the above, there remains a need for systems and methods that can accurately detect myocardial disease, such as a acute or chronic ischemia.

SUMMARY

The present disclosure is directed to systems and methods for determining cardiac conditions from electrocardiogram ("ECG") measurements. In particular, the present disclosure describes an approach for delineating cardiac waveforms and identifying characteristic points associated with different phases of cardiac activity that overcomes the limitations of previous threshold-based methods. In addition, a metric is provided that reflects, on a beat-to-beat basis, changes in measured ECG signals over both ventricular depolarization and repolarization. As will be appreciated, such metric accounts for subject and lead selection variability in ECG signals, representing an efficient and accurate indicator for the onset of an acute ischemic episode or the progression of an ongoing ischemic episode.

In one aspect of the present disclosure, a system for determining a cardiac condition of a subject is provided. The system includes one or more electrodes configured to sense a cardiac activity of a subject, and a processor programmed to receive ECG signals acquired using the one or more electrodes, and analyze the ECG signals to delineate cardiac waveforms on a beat-to-beat basis. The processor is also programmed to identify, in the delineated cardiac waveforms, characteristic points associated with different phases of cardiac activity, and for each delineated cardiac waveform, compute an ischemic index using the ECG signals corresponding to a ventricular depolarization period and a ventricular repolarization period, wherein the ventricular depolarization period and the ventricular repolarization period are defined by the identified characteristic points. The processor is further programmed to determine a cardiac condition of the subject using each computed ischemic index, and generate a report indicative of the cardiac condition of the subject.

In another aspect of the present disclosure, a method for determining a cardiac condition of a subject is provided. The method includes acquiring ECG signals using one or more electrodes configured to sense a cardiac activity of a subject, and analyzing the ECG signals to delineate cardiac waveforms on a beat-to-beat basis. The method also includes identifying, in the delineated cardiac waveforms, characteristic points associated with different phases of cardiac activity, and for each delineated cardiac waveform, computing an ischemic index using the ECG signals corresponding to a ventricular depolarization period and a ventricular repolarization period, wherein the ventricular depolarization period and the ventricular repolarization period are defined by the identified characteristic points. The method further includes determining a cardiac condition of the subject using each computed ischemic index.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5A is a graphical illustration showing ischemic index changes in ECG signals from body surface leads following induced myocardial ischemia.

FIG. 5B is a graphical illustration showing ischemic index changes in ECG signals from coronary sinus leads following induced myocardial ischemia.

FIG. 5C is a graphical illustration showing ischemic index changes in ECG signals from left ventricle leads following induced myocardial ischemia.

FIG. 5D is a graphical illustration showing ischemic index changes in ECG signals from right ventricle leads following induced myocardial ischemia.

FIG. 5E is a graphical illustration showing ischemic index changes in ECG signals from triangular right ventricle-coronary sinus leads following induced myocardial ischemia.

FIG. 6A is a graphical illustration showing the probability of observing a statistically significant change in a body-surface lead given a statistically significant change in the corresponding intra-cardiac leads.

FIG. 6B is a graphical illustration showing the probability of observing a statistically significant change in an intra-cardiac lead configuration given a statistically significant change in the corresponding intra-cardiac leads.

FIG. 6C is a graphical illustration showing the conditional probability that the ischemic index following myocardial ischemia exceeds a baseline value given an increase observed in any other lead configuration.

FIG. 8A is a graphical illustration showing dynamic ischemic index changes in ECG signals from body surface leads preceding a ventricular tachy-arrhythmic event.

FIG. 8B is a graphical illustration showing ischemic index changes in ECG signals from coronary sinus leads preceding a ventricular tachy-arrhythmic event.

FIG. 8C is a graphical illustration showing ischemic index changes in ECG signals from left ventricle leads preceding a ventricular tachy-arrhythmic event.

FIG. 8D is a graphical illustration showing ischemic index changes in ECG signals from right ventricle leads preceding a ventricular tachy-arrhythmic event.

FIG. 8E is a graphical illustration showing ischemic index changes in ECG signals from triangular right ventricle-coronary sinus leads preceding a ventricular tachy-arrhythmic event.

DETAILED DESCRIPTION

Figure 1A:
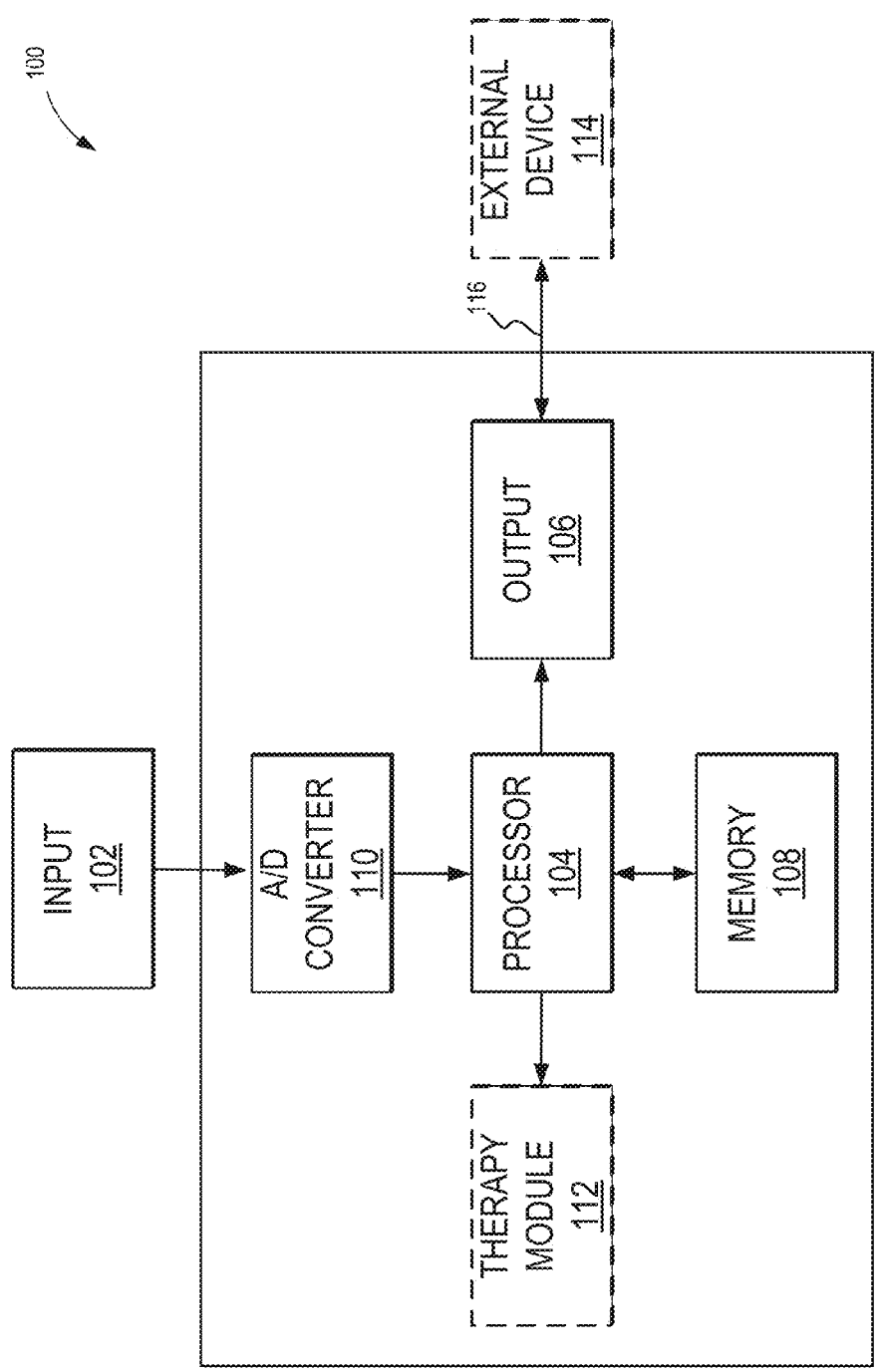
FIG. 1A is a block diagram of an example monitoring system, in accordance with aspects of the present disclosure.

The present disclosure is directed to systems and methods for determining and in some aspects controlling cardiac conditions using electrocardiogram ("ECG") measurements. In particular, the present disclosure recognizes that certain long-term or acute cardiac conditions, such as myocardial ischemia or ventricular tachycardia events, may be determined by quantifying changes in ECG signals. Therefore, a novel detection approach based on a robust ECG delineator is provided, one which accurately estimates characteristic points associated with different phases of cardiac activity. In addition a metric is provided that can reflect, on a beat-to-beat basis, changes associated with cardiac signals over both the ventricular depolarization period and the ventricular repolarization period.

Turning to FIG. 1, block diagram of an example monitoring system 100, in accordance with aspects of the present disclosure, is shown. The monitoring system 100 may be any device, apparatus or system configured for determining and/or controlling a condition of a subject, such as myocardial ischemia. In some aspects, the monitoring system 100 may operate as part of, or in collaboration with a computer, system, device, machine, or mainframe, server, and may be portable or wearable. For example, the monitoring system 100 may be a mobile phone, a tablet, as well as an implantable or other personal electronic device. In this regard, the monitoring system 100 may be any general computing device that can integrate a variety of software and hardware capabilities and functionalities. In some aspects, the monitoring system 100 may transmit data or signals using wireless communication, such as Bluetooth, or other communication protocols.

As shown in FIG. 1, the monitoring system 100 may be configured to include at least an input 102, a processor 104, an output 106, a memory 108, an analog-to-digital ("A/D") converter 110 and optionally a therapy module 112. The input 102 may include any number of sensors configured to obtain various physiological signals or data from a subject, including signals or data associated with cardiac activity. Specifically, the sensors may be arranged upon a surface or within the anatomy of a subject, in any desired configuration. In some aspects, the input 102 can include unipolar or bipolar leads configured to receive cardiac activity data, or "ECG data" or "ECG signals" data, from surface or implanted or implantable electrodes. As will be described, in some aspects, input 102 can advantageously include intra-cardiac electrodes positioned within or in proximity to the right atrium, the right ventricle, the left ventricle or coronary sinus of a subject's heart. However, it may be appreciated that other locations for the intra-cardiac electrodes, and other electrodes, may also be possible.

Sampled signals or data obtained from input 102 may then be converted to digital signals using the A/D converter 110, and then communicated to the processor 104 for processing and analysis using, for example, instructions stored in the memory 106. In particular, signals may be sampled continuously or intermittently by the processor 104. In other aspects, sampled or processed signals or data may be stored within and retrieved from the memory 106.

In accordance with aspects of the present disclosure, the processor 104 is configured analyze ECG signals received from a subject by delineating cardiac waveforms and characteristics therein on a beat-to-beat basis. In particular, the processor 104 may be configured to apply a detection algorithm to identify waveforms or features in acquired ECG signals, such as the QRS complex, or more specifically the R-wave, as well as other features. The processor 104 may also be configured to refine initial waveform or feature detections, for example, by using a template-matching alignment algorithm for detected QRS complexes, and/or by eliminating abnormal beats, such as premature ventricular complexes or aberrantly conducted beats. The processor 104 is also configured to identify, in the delineated cardiac waveforms, characteristic points associated with different phases of cardiac activity. This includes applying a wavelet transform ("WT") delineator in order to accurately identify characteristic points and waveform boundaries.

In accordance with aspects of the present disclosure, the processor 104 is also configured to compute an ischemic index for each delineated cardiac waveform, using characteristic points identified therein. As will be described, computations of an ischemic index are advantageously performed using ECG signals corresponding to the ventricular depolarization and repolarization periods. However, the processor 104 may be configured to compute any metric or index associated characteristic points and waveform boundaries corresponding to the cardiac cycle, and identified as described. For instance, in some aspects, the processor 104 may be configured to compute a median or a mean of ischemic index values obtained over multiple cardiac cycles. In other aspects, the processor 104 may be configured to compute the medial or mean of ischemic index values over a predetermined time window. For example, the predetermined time window may be 1 minute, although other values may be possible. The processor 104 may further be configured to determine a long-term or acute cardiac condition of the subject using computed metrics or indices, including the ischemia index. For example, the processor 104 may be configured to determine a myocardial ischemia, or a ventricular tachyarrhythmia.

As shown in FIG. 1A, the processor 104 is in communication with an output 108 configured to provide a report using information relayed by the processor 104. For instance, the output 106 may display raw or processed ECG signals or any information derived therefrom, in real-time or near real-time, via a display or printing system. In some aspects, the output 106 may also communicate data or information to an external device 114 via wired or wireless communication 116. For example, the external device 114 may be a mobile computing system, including a smartphone, a tablet, a network, a cloud server, and so forth.

The generated report may include information regarding delineated cardiac waveforms, and characteristic points associated with different phases of cardiac activity, as well as computed ischemic index values and other indicators. In some aspects, the report be in the form of an audio or visual signal or indicator informing or alerting a user regarding a determined cardiac condition.

As shown in FIG. 1A, the monitoring system 100 may optionally include a therapy module 112, in communication with the processor 104, and configured for to deliver a timely therapy as a result of a determined acute or long-term cardiac condition. For instance, the therapy module 112 may, upon receiving instructions from the processor 104, generate and deliver an electrical signal or stimulation to a subject via electrodes arranged about the subject. As such, the monitoring system 100 may include capabilities associated with pacemakers or defibrillators. Alternatively, the therapy module 112 may be configured to deliver one or more pharmaceutical agent or treatment to the subject. For example, such pharmaceutical treatment may be intended to mitigate or counteract effects or symptoms of a determined medical condition, such as a myocardial ischemia.

Figure 1B:
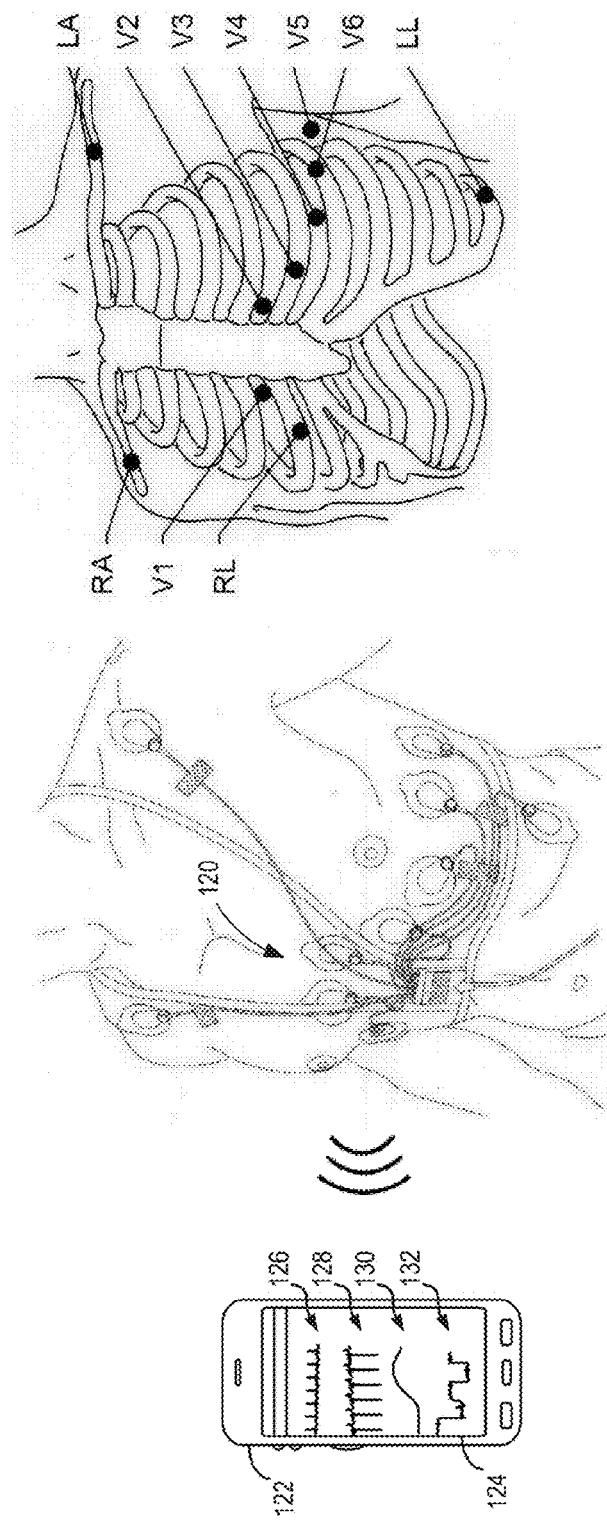
FIG. 1B is a schematic illustration of an example monitoring system such as described in the present disclosure for use with a mobile device.
Figure 14:
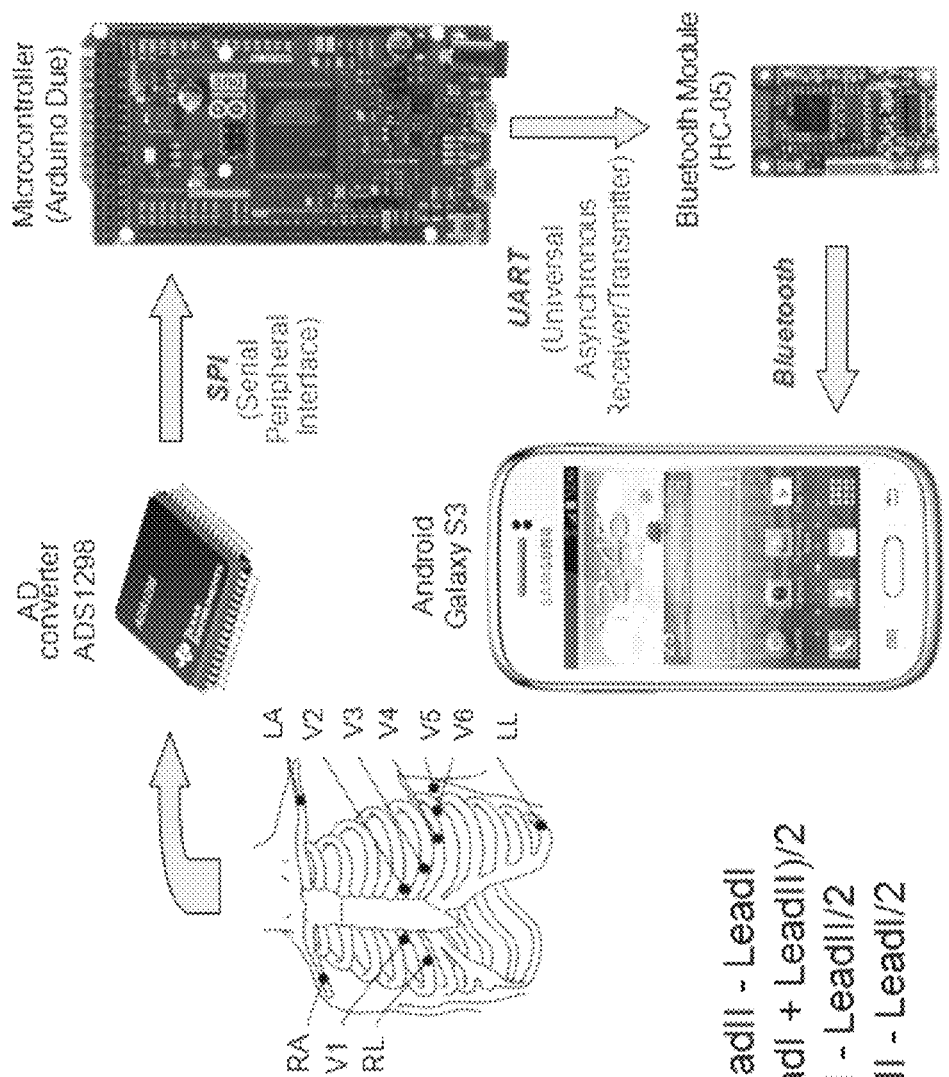
FIG. 14 shows an example communication diagram, in accordance with aspects of the present disclosure.

By way of a non-limiting example, a 12 lead ECG acquisition, display, and analysis system, for use in accordance with aspects of the present disclosure, is shown in FIG. 1B. The system may include a multi-channel ECG module 120 (such as a PSL-ECG 12MD from Physiolab) including an A/D converter (such as an ADS1298 from Texas Instruments), a microcontroller or processor (such as a Due from Arduino), an output (such as a Bluetooth communications UART converter, such as a HC-05 from Guangzhou HC Information Technology Co., Ltd), as shown in FIG. 14. As shown in FIG. 1B, the ECG module 120 can communicate wirelessly, for example using Bluetooth communication, with an external device 122, such as mobile device, smartphone, and so forth.

Figure 15:
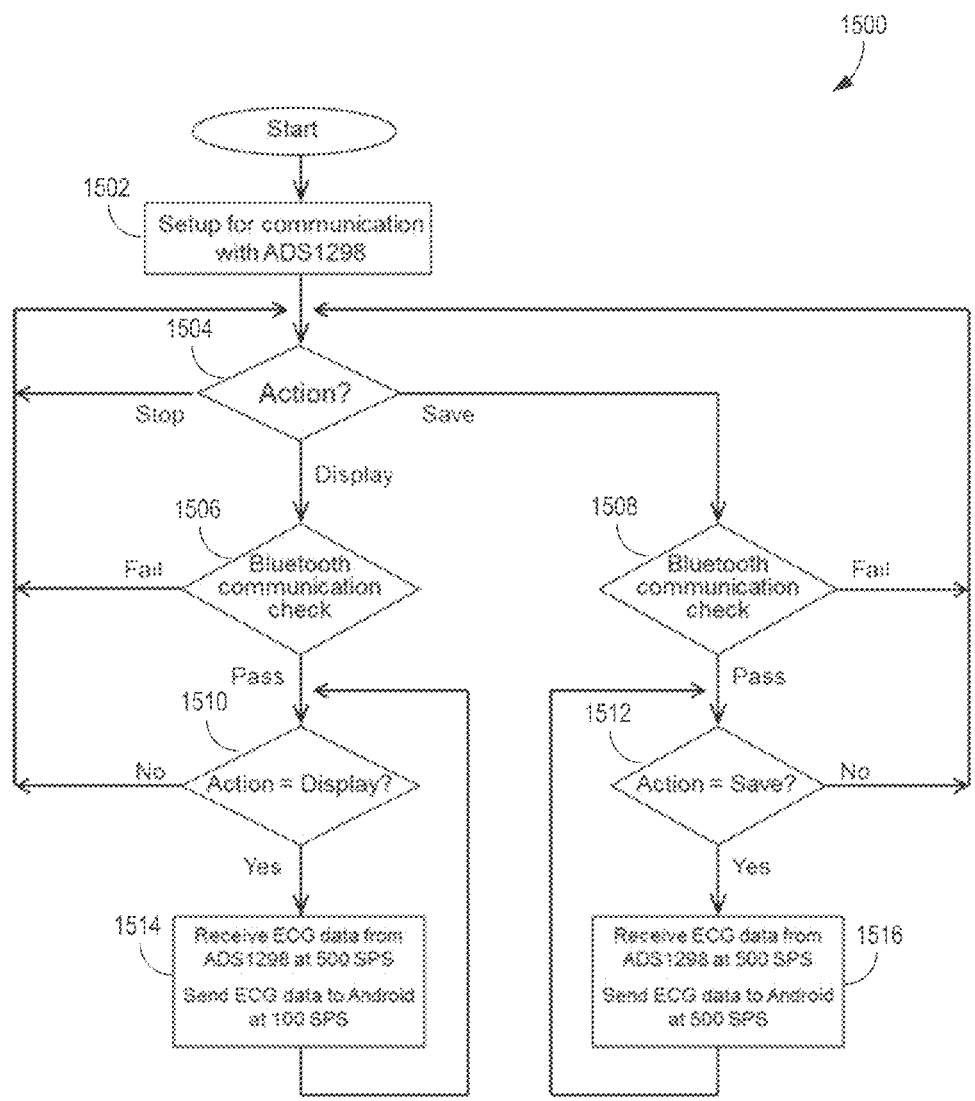
FIG. 15 is a flowchart setting forth steps of a communication process, in accordance with aspects of the present disclosure.

Turning to FIG. 15, a block diagram setting forth steps of a communication process 1500 carried out by a microcontroller embedded software, in accordance with aspects of the present disclosure, is shown. The process 1500 begins at process block 1502 where the microcontroller completes a setup for communication with an A/D converter and a Bluetooth module. The microcontroller repeatedly checks at decision blocks 1504, 1510, and 1512 a user's input, for example, a request to display, save or stop, and responds to the request. The microcontroller further verifies Bluetooth communication at decision blocks 1560 and 1508. When a display/save request is received, the microcontroller sends ECG signals, and other data or information, at 100 or 500 samples per second, as indicated by process blocks 1514 and 1516, respectively, although other higher sample rates may also be possible or desired.

By way of example, 10 ECG electrodes (RL, LL, RA, LA, V1-V6) are illustrated in FIG. 1B as connected to the ECG module 120. In operation, the A/D converter amplifies and digitizes 8 leads (I, II, and V1-V6), for example, simultaneously at 500 samples/sec or higher. A Wilson's central terminal ((LA+RA+LL)/3) may be used as a reference potential for the precordial leads. The ECG module 120 processor can communicate with the A/D converter via, for example, a wired communications link or connection and coordinate communication of acquired data to the external device 122 via the output, using Bluetooth or other wireless communications protocols. For example, the digitized 24 bit resolution signals may be transferred to the ECG module 120 processor, which reduces the resolution to 16 bits in order to reduce the number of errors during wireless data transmission to the external device 122. The data or information received by the external device 122 may be processed, in accordance with aspects of the present disclosure, and then provided to a user or clinician via a display and associated user interface 124. In some aspects, the external device 122 may calculate the 12 lead ECG signals (I, II, III, aVR, aVL, aVF, and V1-V6) from the 8 leads.

In other aspects, the external device 122 may calculate ischemic index values, or other indices, metrics or information determined therefrom obtained using body surface or intra-cardiac electrodes, or combinations thereof. As illustrated in FIG. 1, the external device 122 may display signals from multiple leads at any given time, such as a first ECG signal 126 and a second ECG signal 128, as well as an ischemic index 130, or respiration rate 132, according to pre-programmed or user selections.

Figure 10A:
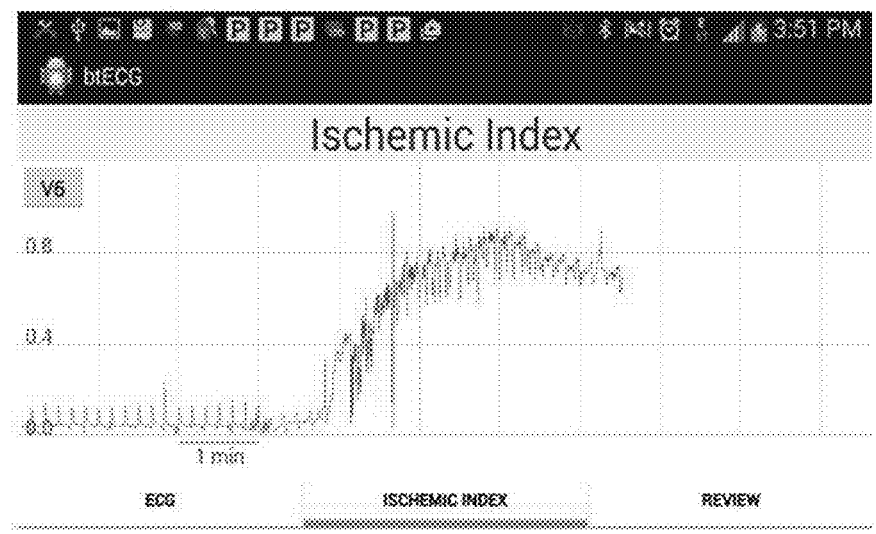
FIG. 10A is an example output of a mobile device, in accordance with aspects of the present disclosure, illustrating time evolution of an ischemic index from lead V6 computed on a beat-to-beat basis during myocardial infarction.
Figure 10B:
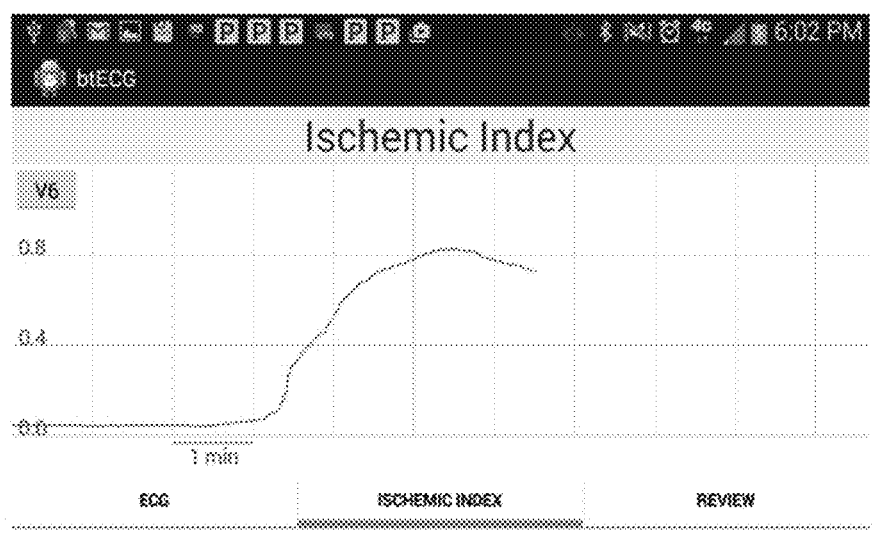
FIG. 10B is another example output of a mobile device, in accordance with aspects of the present disclosure, illustrating the time evolution of a median ischemic index from lead V6 computed over a 1 minute running window during myocardial infarction.
Figure 11A:
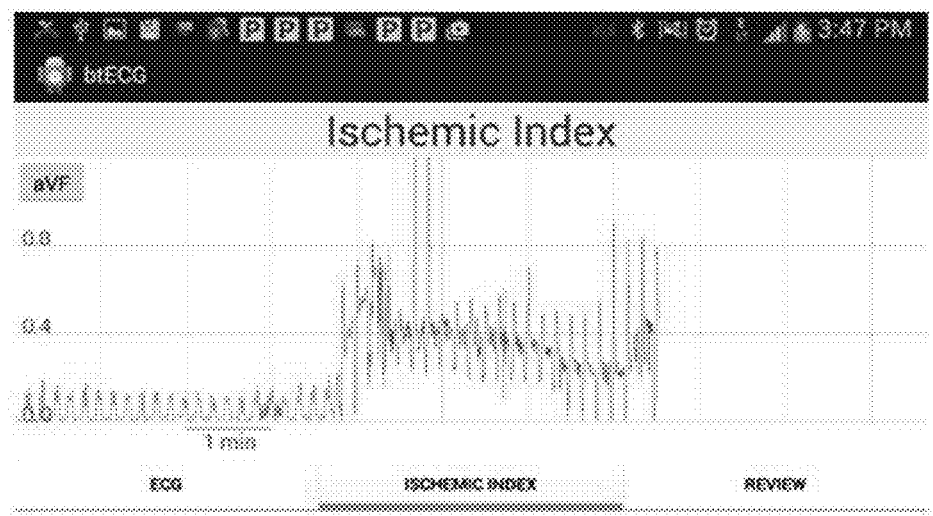
FIG. 11A is another example output of a mobile device, in accordance with aspects of the present disclosure, illustrating time evolution of an ischemic index from lead aVF computed on a beat-to-beat basis during myocardial infarction.
Figure 11B:
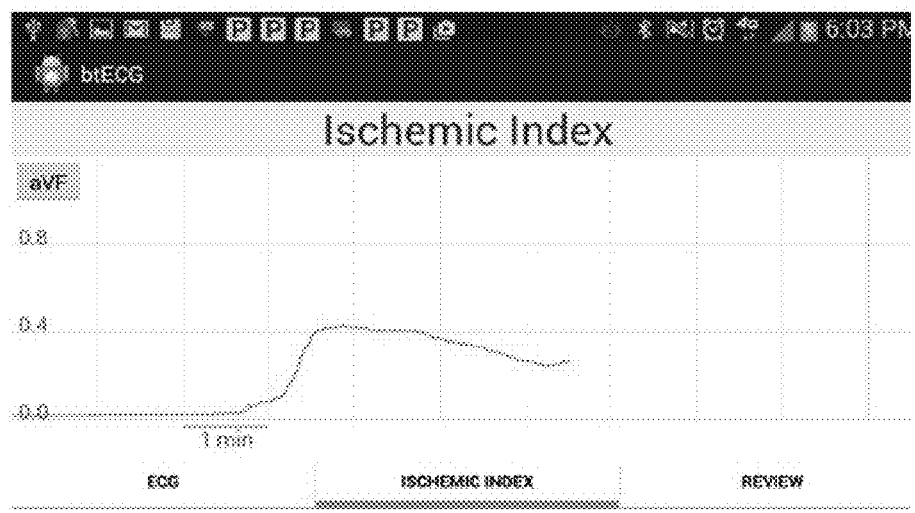
FIG. 11B is another example output of a mobile device, in accordance with aspects of the present disclosure, illustrating the time evolution of a median ischemic index from lead aVF computed over a 1 minute running window during myocardial infarction.
Figure 12A:
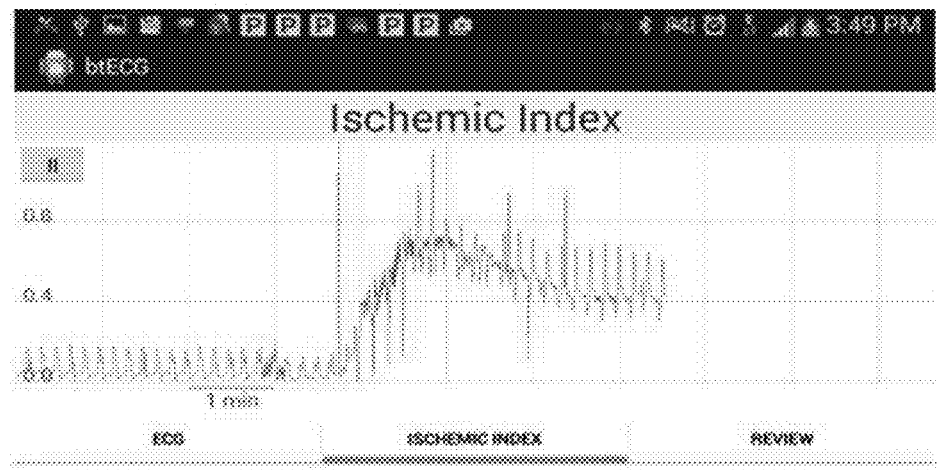
FIG. 12A is another example output of a mobile device, in accordance with aspects of the present disclosure, illustrating time evolution of an ischemic index from lead II computed on a beat-to-beat basis during myocardial infarction.
Figure 12B:
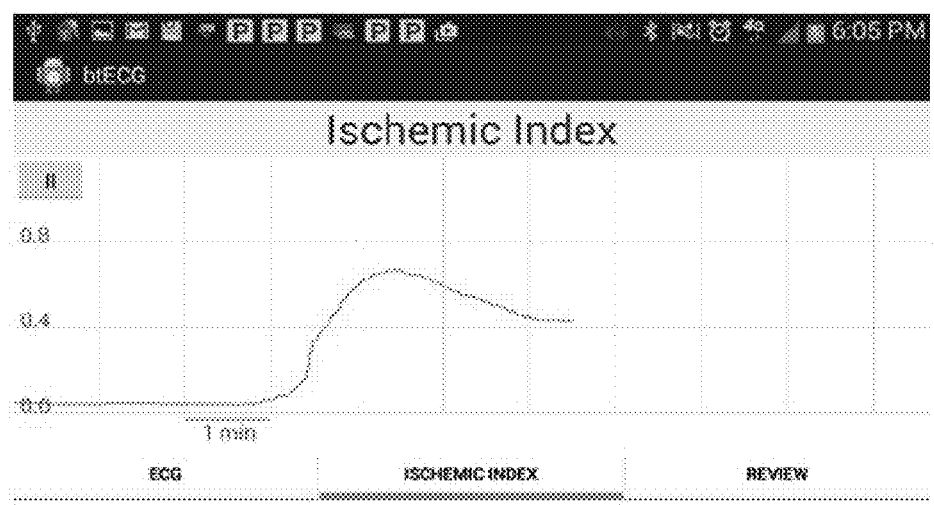
FIG. 12B is another example output of a mobile device, in accordance with aspects of the present disclosure, illustrating the time evolution of a median ischemic index from lead II computed over a 1 minute running window during myocardial infarction.
Figure 13A:
FIG. 13A is another example output of a mobile device illustrating ventricular tachycardia during myocardial infarction captured using lead II.
Figure 13B:
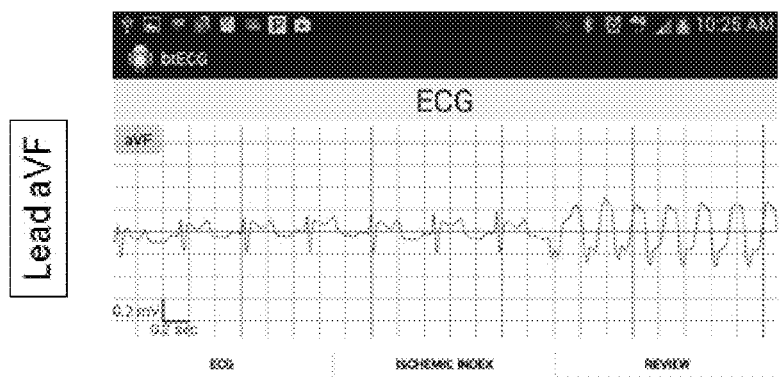
FIG. 13B is another example output of a mobile device illustrating ventricular tachycardia during myocardial infarction captured using lead aVF.
Figure 13C:
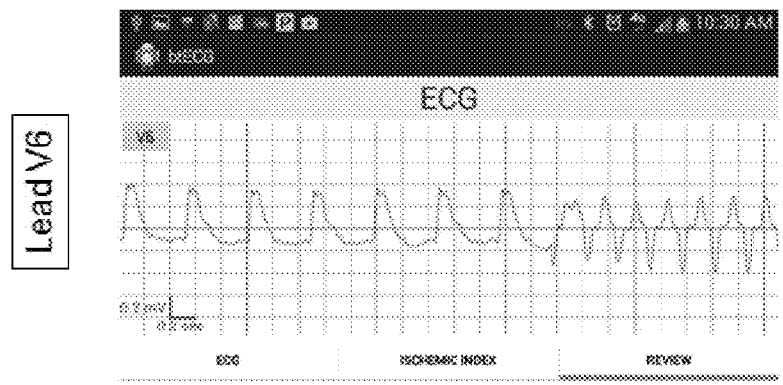
FIG. 13C is another example output of a mobile device illustrating ventricular tachycardia during myocardial infarction captured using lead V6.
Figure 16:
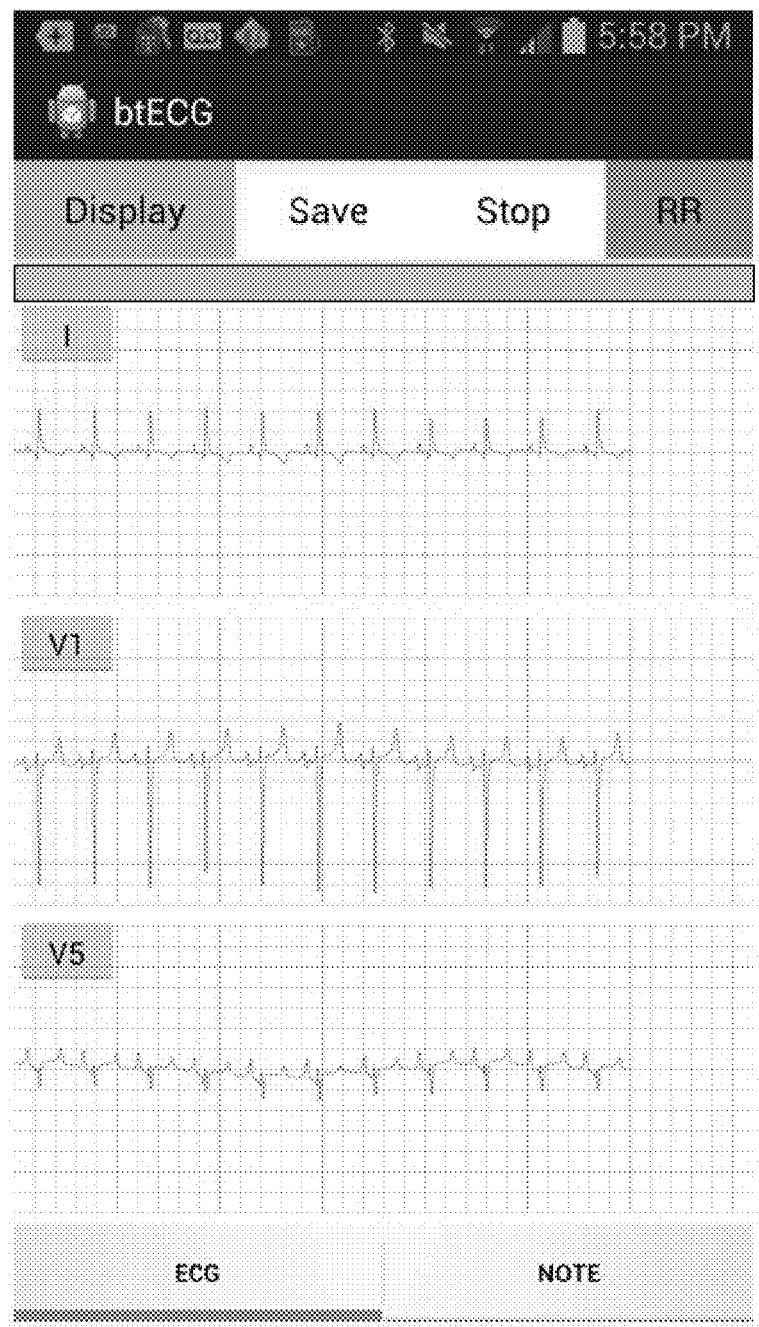
FIG. 16 is another example output of a mobile device showing cardiac signals captured using leads I, V1 and V5.

By way of example, FIGS. 10A and 10B show an output of an Android external device, depicting time evolution of an ischemic index estimated, in accordance with aspects of the present disclosure, before and following myocardial infarction. Specifically, FIG. 10A shows the ischemic index obtained using signals from aV6 lead and computed on a beat-to-beat basis. FIG. 10B shows the median value of ischemic index values computed over a 1 minute running window of FIG. 10A. Similarly FIGS. 11A and 11B, respectively, FIGS. 12A and 12B depict the ischemic index computed on a beat-to-beat basis, and over a 1 minute running window, from data captured using leads aVF (FIGS. 11A and 11B) and II (FIGS. 12A and 12B), respectively. FIG. 16 shows another example of body-surface ECG signals captured using an Android mobile device from leads V5, V1 and I.

Figure 17:
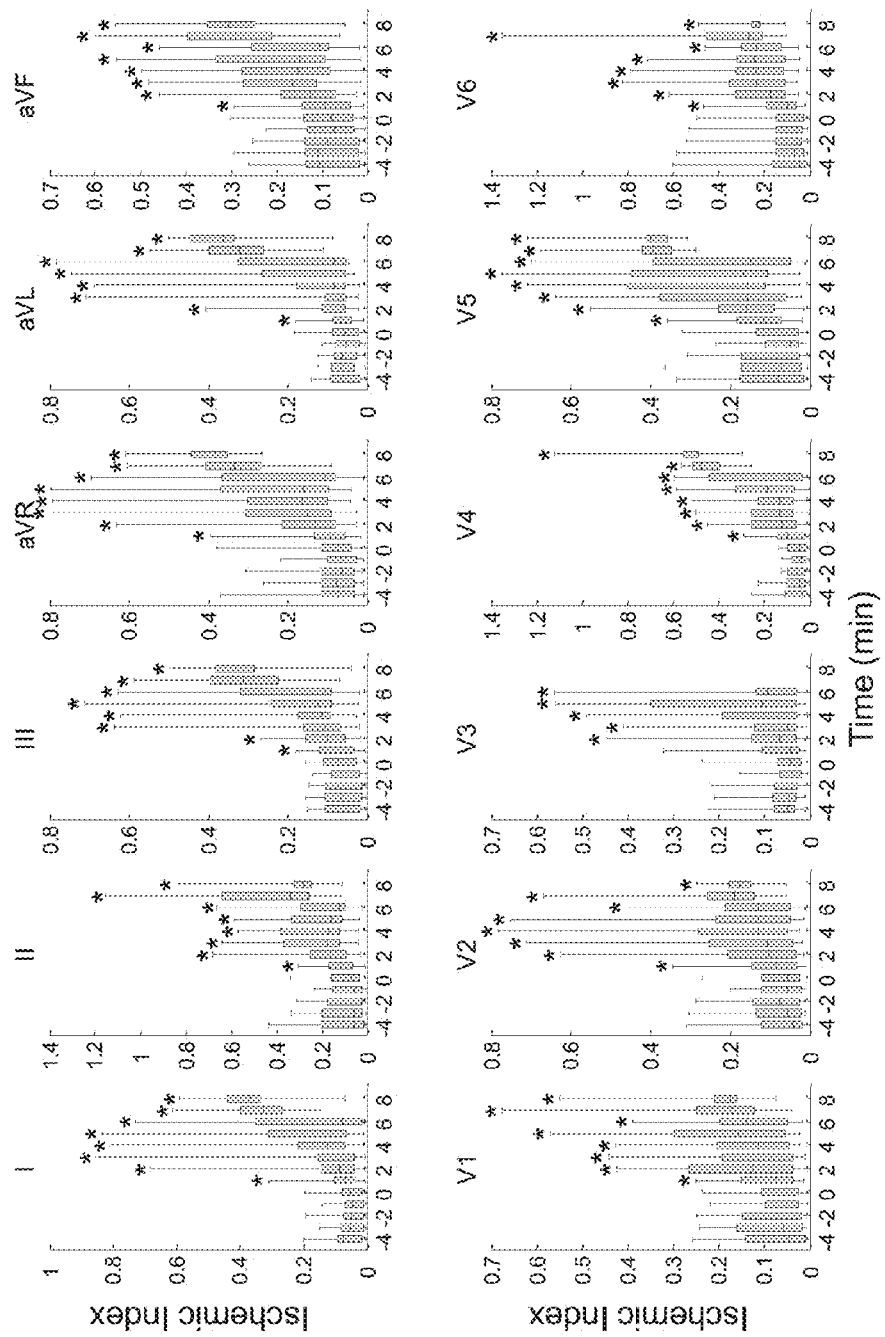
FIG. 17 is a graphical illustration depicting ischemic index values, from multiple leads, obtained on a mobile device following myocardial infarction.
Figure 18:
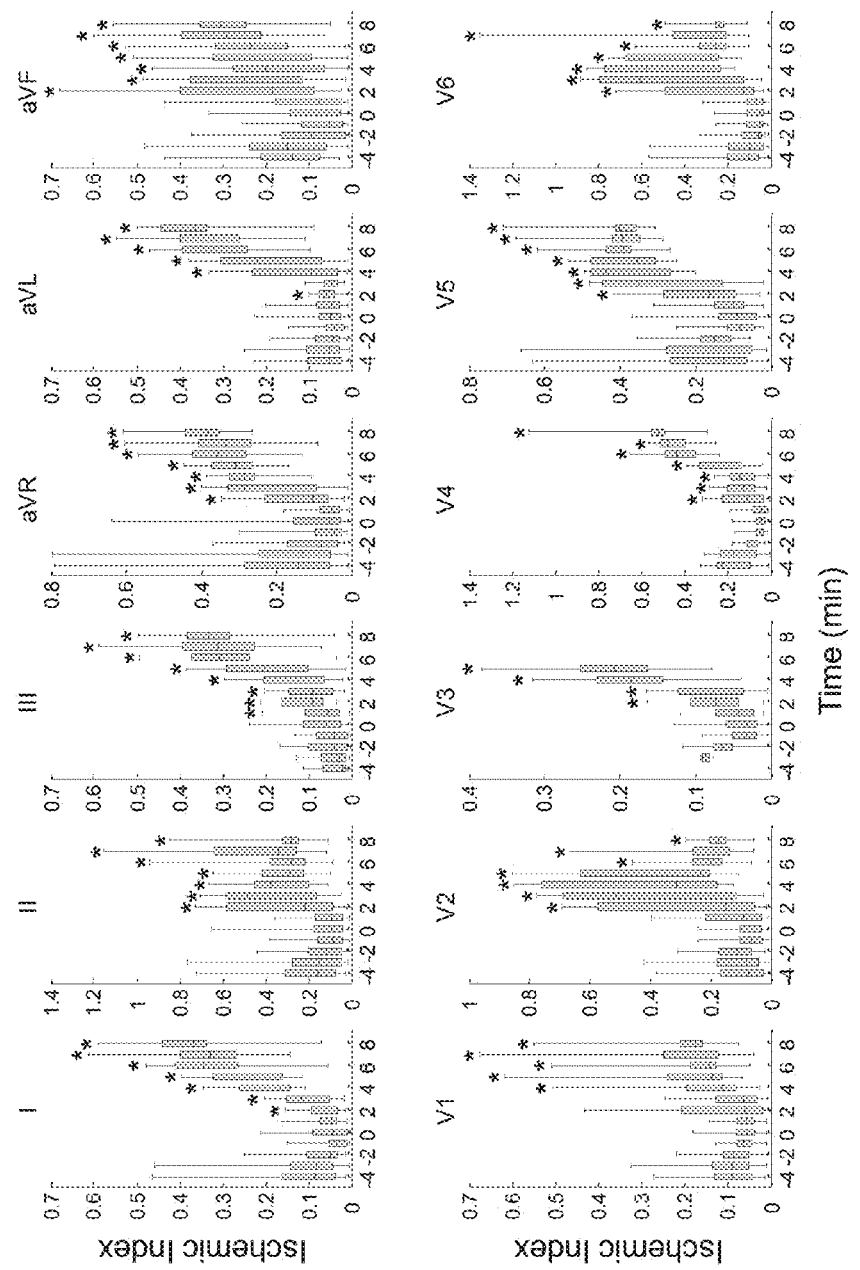
FIG. 18 is another graphical illustration depicting ischemic index values, from multiple leads, obtained on a mobile device following myocardial infarction and preceding ventricular tachycardia.

As another example, FIGS. 17 and 18 ischemic index estimations using an Android mobile device. Specifically, FIG. 17 summarizes ischemic index values from multiple leads obtained using the mobile device before and following myocardial infarction, while FIG. 18 summarizes ischemic index values from multiple leads obtained using the mobile device following myocardial infarction and preceding ventricular tachycardia. The ischemic index was estimated on a beat-by-beat basis and each bar graph in FIGS. 17 and 18 represents the 5, 25, 50, 75 and 95 percentiles of the values of the ischemic index for one minute across all animal subjects. The Kruskal-Wallis test was used for statistics, and an asterisk on a bar graph in FIGS. 17 and 18 represented significantly elevated values of the ischemic index compared to the baseline, that is before occlusion, indicated as time equals 0.

Figure 2:
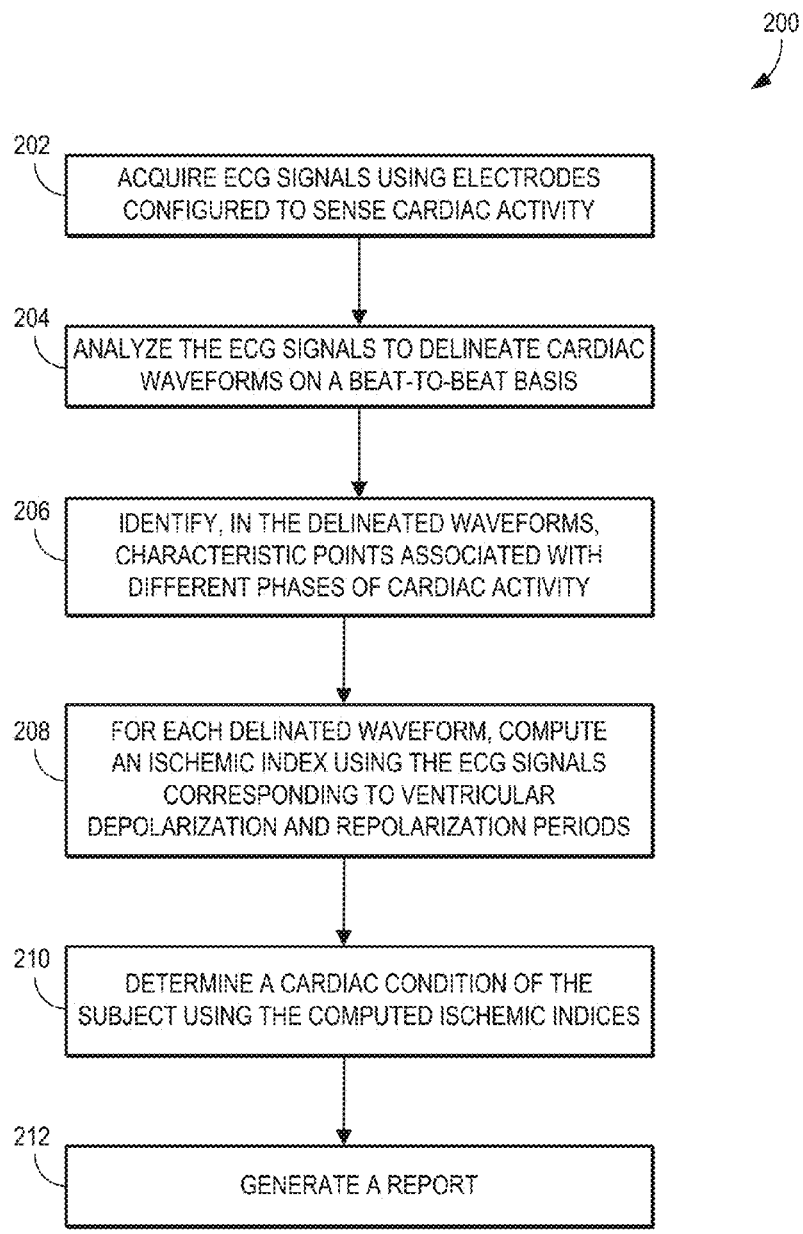
FIG. 2 is a flowchart setting forth steps of a process for determining a cardiac condition of a subject, in accordance with aspects of the present disclosure.

Turning to FIG. 2, a flowchart is shown setting forth steps of a process 200 for determining a cardiac condition of a subject, in accordance with aspects of the present disclosure. Steps of process 200 may be carried out using any devices or systems, for example, such as the monitoring system 100 described with reference to FIG. 1A.

The process 200 may begin at process block 202 where by ECG signals are acquired using at least one electrode configured to sense a cardiac activity of a subject. As described, the ECG signals may be obtained using any combination of body surface or implantable electrodes, such as intra-cardiac electrodes. At process block 204, ECG signals acquired from a subject are analyzed by delineating cardiac waveforms on a beat-to-beat basis. As describes, this includes applying a detection algorithm to identify waveforms or features in acquired ECG signals, such as the QRS complex, or more specifically the R-wave, as well as other features, such as the P-wave, T-wave. In some aspects, initial waveform or feature detected at process block 206 may be refined. That is, a subset of initially detected waveforms or features may be utilized in further analysis. For example, this can include using a template-matching alignment algorithm for detected QRS complexes, and/or eliminating abnormal beats, such as premature ventricular complexes or aberrantly conducted beats.

At process block 206, characteristic points associated with different phases of cardiac activity may be identified in the delineated cardiac waveforms. By way of example, characteristic points may include the onset or offset of the P-wave, the T-wave, the QRS complex, and so forth. In accordance with aspects of the present invention, and in recognizing the challenges of threshold-based methods, a wavelet transform ("WT") technique may be utilized at process block 206 to accurately identify characteristic points and waveform boundaries. In particular, a WT delineator decomposes a given signal by using combination of a set of basis functions obtained by dilation and translation of a single prototype wavelet. In such time-resolution description of the signal, higher frequency components are characterized by the coefficients corresponding to narrower basis functions resulting from lower scale factors, and vice versa.

By way of example, for each beat, a dyadic wavelet transform of a delineated ECG waveform may be estimated for the first 5 scales, for instance. Although it may be appreciated that other scales can be utilized, most or a substantial energy of the waveform lies in the first 5 scales. Then, a quadratic spline may be used as a prototype wavelet that corresponds to a derivative of a low-pass smoothing function. This ensures that the wavelet coefficients are proportional to the derivative of the filtered version of the signal with a smoothing impulse response at each scale. This approach allows the identification of significant points in an ECG signal using the information of local maxima, minima, and zero crossings of the WT coefficients at different scales.

Once WT coefficients are estimated, a search window relative to an identified R-wave, and depending on the R-wave to R-wave interval, may be defined. The number and polarity of the maximum modulus of WT within the window and across different scales reflects the characteristic points corresponding to the delineated ECG waveforms. To accommodate signals associated with intra-cardiac electrodes, above steps may be modified to start with scale $2^3$ for delineated P-waves and T-waves. In some aspects, reduced amplitude thresholds proportional to the root-mean-square value of the WT may be utilized at the corresponding scales. To accommodate the loss of time resolution in the growing scales, a multi-scale approach for the P-wave, QRS complex and T-wave delineation may be utilized. For instance, if a waveform boundary is not identified at a specific scale, the above process may be repeated over higher scales.

At process block 208, an ischemic index may be computed for each delineated cardiac waveform. In accordance with aspects of the present disclosure, each ischemic index is computed using ECG signals corresponding to the ventricular depolarization period and the ventricular repolarization period of respective cardiac waveform, where each period is defined or determined using the characteristic points obtained at process block 206. Specifically, the ischemic index is computed by taking the absolute value of the ratio of an ST height to the amplitude of a QR segment, where the ST height is defined as the mean ST amplitude over all ECG data points between the offset of the QRS complex and the onset of T-wave whose values are in excess, that is, greater (ST elevation), or smaller (ST depression), than an isoelectric baseline. However, other metrics or indices associated characteristic points and waveform boundaries, as identified at process block 206, may be computed at process block 208. For example, in some aspects, the real value (positive or negative) of the ratio between the ST height to the amplitude of a QR segment may be used instead of the absolute value. In another example, the medial ST amplitude may be used to compute the ischemic index.

In case that the amplitude of a signal at the offset of the QRS complex has opposite polarity compared to the onset of the T-wave, in computing an ischemic index, the longer segment in the QRS offset to T-wave onset interval) may be used to estimate the ST height. Also, the isoelectric baseline may be obtained from signals in the PR segment, which is interval following the P-wave and preceding the onset of the QRS complex. However, in some aspects, signals in the TP segment, describing the interval following the T-wave and preceding the next P-wave, may be considered as the isoelectric baseline. This is because the PR segment may not flat, as is the case for measurements obtained using coronary sinus leads, for example. As may be appreciated, the above-defined ischemic index is independent of signal amplitude variability occurring between different measurement sensors. In some aspects, a median or a mean of ischemic index values, obtained over multiple cardiac cycles may be computed. In particular, the median or mean may be obtained by utilizing ischemic index values in a pre-determined time window, for example, of 1 minute, although other values may be possible.

Then, at process block 210, a long-term or acute cardiac condition of the subject may be determined using computed metrics or indices, including the ischemia index. For example an acute or long-term myocardial ischemia, or a ventricular tachyarrhythmia event may be determined by comparing computed metrics or indices with baseline, or reference values. In some aspects, such baseline or reference values, for example, stored in a memory, which may be dependent upon the characteristics of the subject, or a population, or may be dependent upon the selection of measurement configuration, electrodes or leads.

Figure 3:
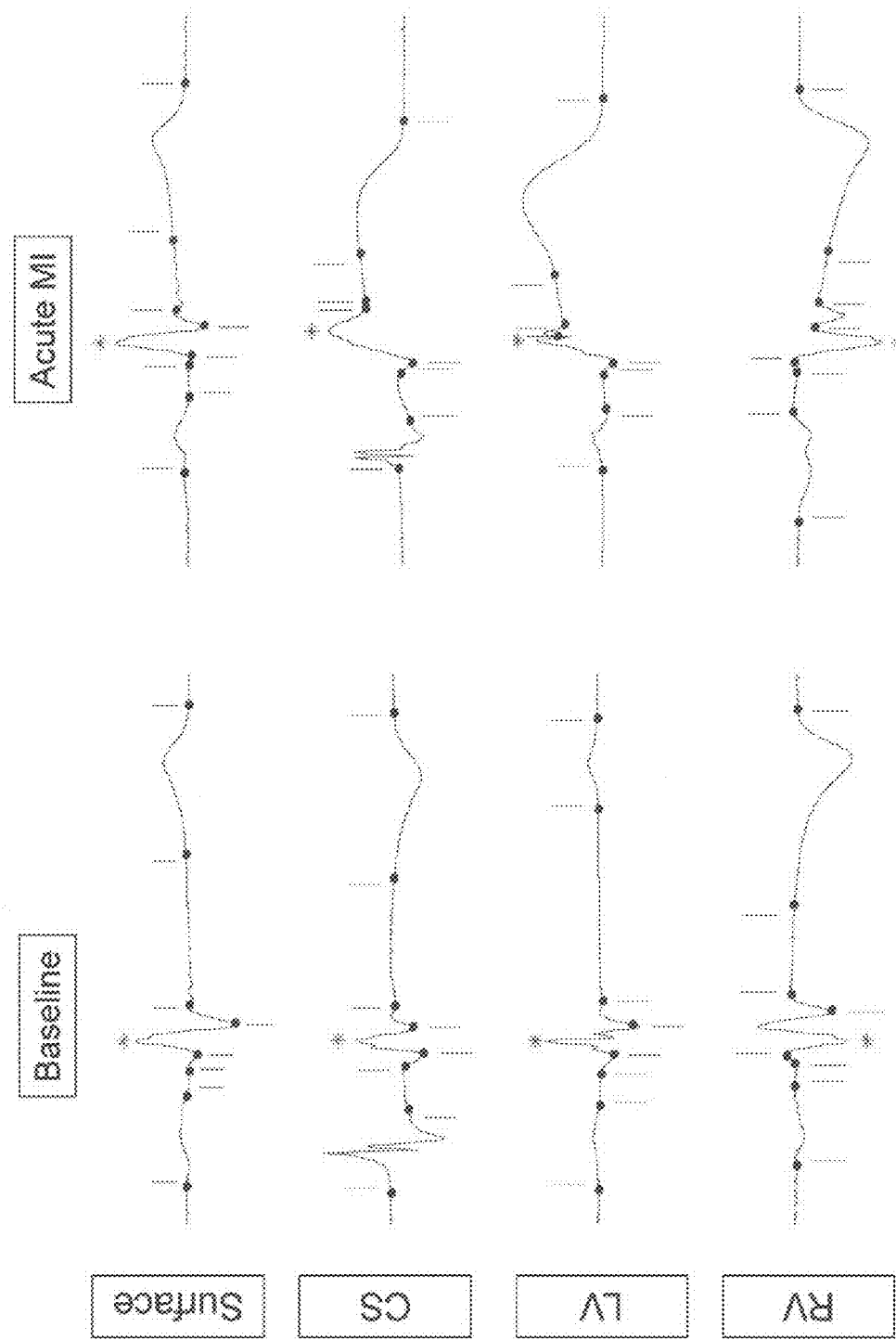
FIG. 3 shows representative body-surface and intra-cardiac electrocardiogram ("ECG") data at baseline and during acute myocardial ischemia delineated in accordance with aspects of the present disclosure.

A report indicative of the cardiac condition of the subject may then be provided, as indicated by process block 212. The report may be in the form of a display of raw or processed ECG signals or any information derived therefrom, in real-time or near real-time, via a display or printing system. In some aspects, a generated report may include information regarding delineated cardiac waveforms, and characteristic points associated with different phases of cardiac activity, as well as computed ischemic index values, for instance, as shown in the example of FIG. 3. In other aspects, the report may be in the form of an audio or visual signal or indicator informing or alerting a user or a physician regarding a determined cardiac condition.

In some aspects, a therapy may be delivered at process block 212, either immediately or periodically, as a result of a determined acute or long-term cardiac condition. For instance, an electrical signal may be generated and delivered to a subject via electrodes arranged about the subject. In addition, one or more pharmaceutical agents or treatments may be delivered to the subject. For example, a pharmaceutical treatment intended to mitigate or counteract effects or symptoms of a determined medical condition, such as a myocardial ischemia, may be delivered at process block 212.

The above-described systems and methods may be further understood by way of examples. These following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, certain lead arrangements and configurations are presented, although it may be understood that other configurations may be possible, and still considered to be well within the scope of the present invention. Likewise, specific process parameters and methods are recited that may be altered or varied based on variables such as signal amplitude, phase, frequency, duration, and so forth.

Example

A large proportion of irreversible myocardial injury and fatal ventricular tachy-arrhythmias occurs in the first hour after coronary artery occlusion. Therefore, early detection of acute myocardial infarction is desirable to help improve clinical outcomes. Hence, a study was conducted to investigate the hypothesis that morphologic analysis of intra-cardiac electrograms can provide a sensitive approach for detecting acute myocardial infarction or myocardial infarction-induced arrhythmia susceptibility.

A robust method was devised for determining the complex annotations of intra-cardiac electrograms, which overcomes potential limitations of established threshold-based methods. Specifically, the inventors recognized that the wavelet transform ("WT") offers simultaneous interpretation of the signal in both time and frequency using a frequency-dependent windowing, which allows high localization in time for high frequency signal components as well as high frequency resolution for low frequency patterns (multi-resolution analysis). Also, in addition to above-described approach for delineating characteristics of electrocardiographic signals, a metric was developed to quantify the ischemia-induced changes in these signals.

Body surface and intra-cardiac electrograms were obtained baseline and following myocardial ischemia in swine. Statistically significant ischemia-induced changes after the initiation of occlusion compared to baseline were detectable within 30 sec in intra-cardiac LV (P<0.0016) and RV-CS (P<0.0011) leads, 60 sec in CS leads (P<0.0002), 90 sec in RV leads (P<0.0020), and 360 sec in body surface electrocardiographic signals (ECGs), (P<0.0022). Intra-cardiac leads exhibited a higher probability of detecting ischemia-induced changes than body surface leads (P<0.0381), and the RV-CS configuration provided the highest sensitivity (96%). 24-hr ECG recordings showed that the ischemic index is statistically significantly increased compared to baseline in Lead I, aVR and all precordial leads (P<0.0388). Finally, we have shown that the ischemic index in intra-cardiac electrograms is significantly increased preceding ventricular tachyarrhythmic events (P<0.0360). As will be shown, the novel method presented is capable of detecting ischemia-induced changes in intra-cardiac electrograms as early as 30 sec following myocardial ischemia, or as early as 12 minutes preceding tachyarrhythmic events.

TABLE 1

Study population characteristics.

| Study | Measures | Baseline | Post-MI | P-value |
|---|---|---|---|---|
| Acute | Number of records | 17 | 17 | |
| | Heart Rate (bpm) | 109.36 ± 12.98 | 110.72 ± 16.09 | 0.65 |
| | PVC occurrence (%) | 0.98 ± 1.34 | 0.82 ± 1.01 | 0.63 |
| pre-VTE | Number of records | 9 | 9 | — |
| | Heart Rate (bpm) | 111.90 ± 15.55 | 106.05 ± 8.26 | 0.25 |
| | PVC occurrence (%) | 0.59 ± 0.68 | 1.44 ± 2.38 | 0.19 |
| Holter | Number of records | 4 | 4 | — |
| | Heart Rate (bpm) | 112.70 ± 7.31 | 151.01 ± 22.42 | 0.12 |
| | PVC occurrence (%) | 0.82 ± 1.22 | 1.65 ± 0.68 | 0.37 |

The total study population included 24 male Yorkshire swine (40-45 kg) that were anesthetized and instrumented. Detailed description of the subjects involved in the study is provided in Table 1.

Each animal was intubated and placed on a mechanical ventilator and anesthesia was maintained with Isoflurane (1.5-5%). Standard ECG electrodes were placed on the animal's limbs and chest. For intra-cardiac recordings, percutaneous vascular access was obtained in the jugular veins and femoral arteries and veins using standard Seldinger techniques. Decapolar catheters were placed under fluoroscopic guidance in the right atrium (RA), right ventricle (RV), coronary sinus (CS), and left ventricle (LV). An inferior vena cava catheter was inserted as a reference electrode for unipolar signals. An arterial line was used to monitor invasive blood pressure. Regional myocardial infarction was induced via balloon occlusion of the proximal left circumflex coronary artery, using standard percutaneous cardiac catheterization techniques. Ischemia has been validated and confirmed by hand injections of contrast into the coronary in which case no-flow as well as electrocardiographic changes were indications of full occlusion. In 4 animals, 24-hr Holter ECG recordings were performed prior and immediately post myocardial ischemia.

Two standard body surface (leads II and V4) and 12 intra-cardiac unipolar electrocardiographic signals (from the CS, LV and RV catheters) were recorded through a Prucka Cardiolab (GE Healthcare, Buckinghamshire, UK) electrophysiology system and digitized at a sampling rate of 1 kHz by a multichannel 16-bit data acquisition card (National Instruments M-Series PCI-6255). The Prucka system provided 16 high fidelity analog output signals with front-end signal conditioning as well as isolation protection of the signal analysis system from defibrillation. Intra-cardiac electrograms (EGMs) were band-pass filtered 0.05-500 Hz, with 60 Hz notch filter and gain 250 V/V, and body surface signals were band-pass filtered 0.05-100 Hz, with 60 Hz notch filter and gain 2500 V/V. Data analysis was performed using custom written software in MATLAB.

Four commonly used threshold-based methods were utilized to detect onset/offset of ECG waveforms for purposes of comparison to the provided approach. Specifically, prior to application of each method, a linear baseline adjustment was performed for each beat. The methods include the (i) Waveform, which determines the onset/offset points at timings corresponding to 5% and 95% of the maximum normalized amplitude; the (ii) Power, which identifies the onset/offset points at time points corresponding to 5% and 95% of the cumulative sum of the signal power; the (iii) Absolute, which is similar to the power approach, except that the threshold is applied to the cumulative sum of the absolute value of the signal; and the (iv) Noise, which estimates the standard deviation of a predefined window (the noise window) of the baseline adjusted waveform, and determines the onset/offset points at timings when the signal exceeds 3 times the standard deviation of the signal in the noise window.

An intra-cardiac ECG delineation algorithm was developed. The algorithm started with obtaining R-wave annotations through a two-step process of first, identifying the R-wave using a QRS detector, and then refining the R-wave location using cross-correlation. Then, for each beat, the dyadic wavelet transform of the signal was estimated for the first five scales. A quadratic spline was used as prototype wavelet, which corresponds to a derivative of a low-pass smoothing function. This ensured that the wavelet coefficients were proportional to the derivative of the filtered version of the signal with a smoothing impulse response at each scale. This approach allowed the identification of significant points in the ECG signal using the information of local maxima, minima and zero crossings of the WT coefficients at different scales.

Once WT coefficients were estimated, a search window relative to the R-wave, and depending on the RR interval, was defined. The number and polarity of the maximum modulus of WT within this window and across different scales reflects the characteristic points corresponding to ECG waveforms. To accommodate the delineation of intra-cardiac signals, the algorithm was modified to start with scale $2^3$ for P-wave and T-wave delineation. Moreover, reduced amplitude thresholds proportional to the root-mean-square value of the WT at the corresponding scales were utilized. To accommodate the loss of time resolution in the growing scales, a multi-scale approach for P, QRS and T wave delineation was devised. If a waveform boundary was not found in a specific scale, the above process was repeated over higher scales.

The ischemic index was computed by taking the absolute value of the ratio of an ST height to the amplitude of a QR segment, where ST height was defined as the mean ST amplitude over all data points from the offset of the QRS complex to the onset of T-wave greater (ST elevation), or smaller (ST depression), than an isoelectric baseline. If the amplitude of a signal at the offset of the QRS complex had opposite polarity compared to the onset of the T-wave, the longer segment in the QRS offset to T-wave onset interval) was used to estimate the ST height. The isoelectric baseline was obtained from signals in the PR segment, which is interval following the P-wave and preceding the onset of the QRS complex. For coronary sinus leads, PR segment is not flat. Hence, for these leads, signals in the TP segment, describing the interval following the T-wave and preceding the next P-wave, were used to determine the isoelectric baseline.

Results are presented as the mean±standard error of normally distributed continuous variables. The duration of the recording and mean heart rate in each data set were compared before and after coronary artery occlusion using the Wilcoxon matched-pairs signed-rank test. A comparison of the percentage of PVCs before and after coronary artery occlusion was performed using a generalized linear model with repeated measurements, and model fitting was performed using a generalized estimating equation ("GEE") method. A Bland-Altman agreement analysis was performed for all ECG leads together and the mean difference and the limits of agreement were used to evaluate degree of agreement between the automated point annotation and the manual reference. A paired non-parametric Wilcoxon signed-rank test was used to evaluate the changes in the ischemic index from baseline to subsequent measurements. Bonferroni correction was used to adjust the significance level for multiple comparisons.

Comparisons between probabilities of detecting a significant change across catheters utilized Kruskal-Wallis ANOVA method. Ischemic index changes from baseline to up to 24 hours post myocardial ischemia were analyzed using linear mixed effects models with random subject intercepts to account for repeated measures. A univariate autoregressive model was used for dynamic regression to describe time-dependent changes of ischemic index at baseline and post myocardial ischemia until sudden cardiac death. Statistical analysis was performed using MATLAB (MathWorks Inc, Natick, Mass.) and STATA (StataCorp LP, College Station, Tex.).

Two expert reviewers provided manual annotations of $P_{onset}$ ($P_{on}$), $P_{offset}$ ($P_{off}$), $QRS_{onset}$ ($QRS_{on}$), $QRS_{offset}$ ($QRS_{off}$), $T_{onset}$ ($T_{on}$) and $T_{offset}$ ($T_{off}$). The manual annotations were used as the gold standard for evaluating each of the delineation methods. Specifically, for each subject, 200 baseline and 200 post-occlusion beats of 2 body-surface, 3 CS, 4 LV and 5 RV leads were given to two independent trained individuals. A graphical user interface was developed to display high resolution ECG beats and to provide a custom designed delineation tool which allowed the user to annotate the waveform of the ECG. Finally, the reference manual waveform annotations for each beat were estimated as the average of the annotations provided by the two reviewers.

FIG. 3 shows representative body-surface and intra-cardiac electrocardiographic beats at baseline (left panels) and during acute myocardial ischemia (MI, right panels) after coronary artery occlusion. For each beat, the manual annotations (averaged over two independent reviewers) are shown by vertical lines and the corresponding wavelet delineation results are depicted by circles. Asterisks indicate R-waves.

Figure 4:
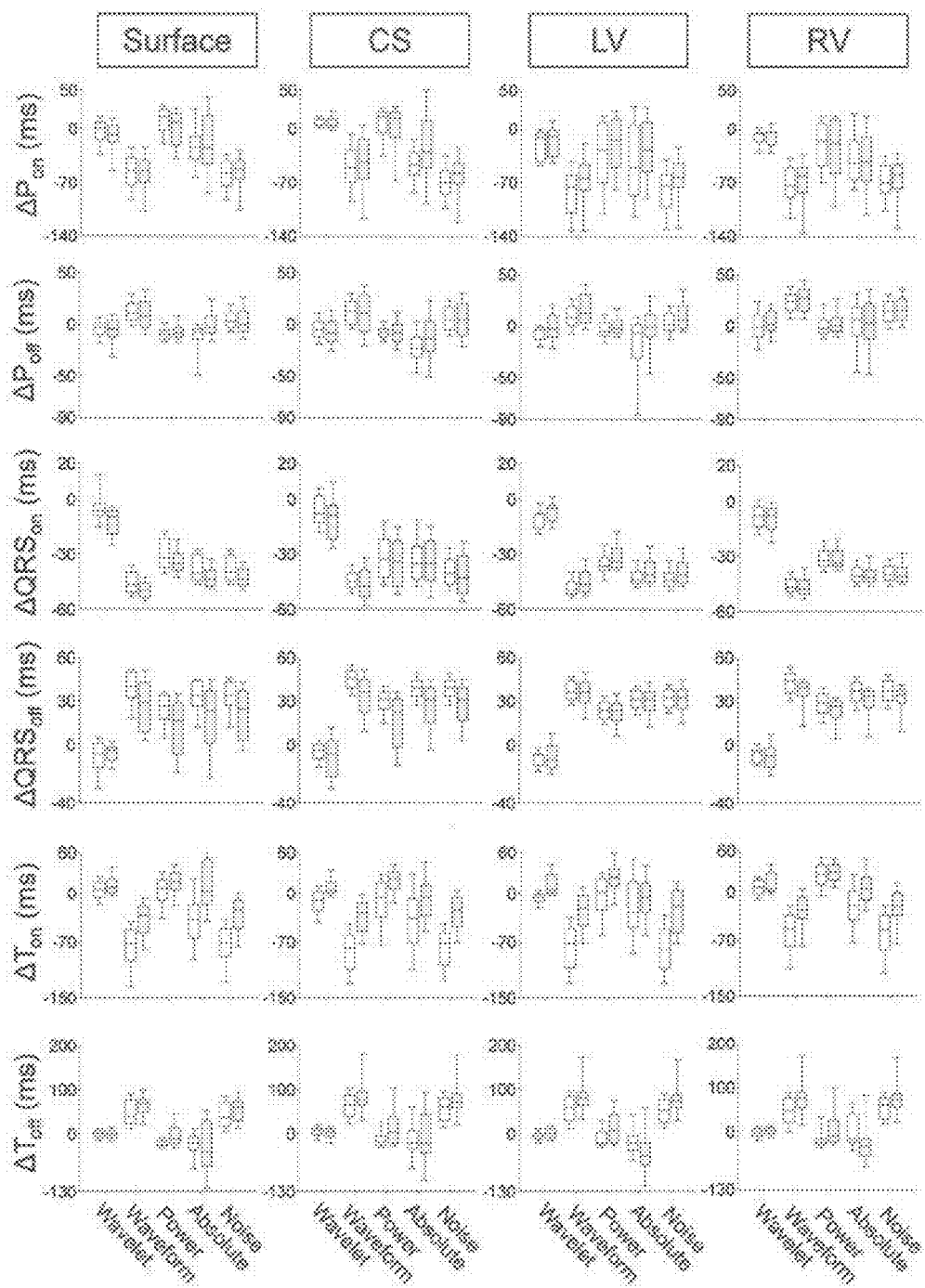
FIG. 4 is a graphical illustration showing features of body surface and intra-cardiac ECG signals delineated using a method, in accordance with the present disclosure, in comparison with other threshold-based techniques.

The accuracy of all five delineation methods in comparison with manual annotation was compared at baseline and after coronary artery occlusion, in both body-surface and intra-cardiac leads. FIG. 4 shows the difference between the automatic annotations obtained by each method and the average of the 2 sets of manual annotations for each ECG waveform. Specifically, the distribution of differences between manual annotations (averaged over two independent reviewers) and those obtained by the wavelet transform, waveform, power, absolute and noise methods are presented for the onset and offset of P-wave, QRS complex and T-wave. Each set of differences have been shown at baseline (white boxes) and following coronary balloon occlusion (gray boxes) for body surface and intra-cardiac CS, LV and RV leads. Data are presented as median (horizontal solid line), 75-25% percentiles (box) and 90-10% percentiles (error bars). Linear regression (each algorithm vs. manual annotation) using all waveform annotations showed that wavelet-based delineations provide the closest estimation to the manual annotations both at baseline and after coronary artery occlusion. Notably, the difference in the non-wavelet based methods appeared more pronounced for points involving the ST segment, i.e. QRS offset and T-wave onset, most likely due to the pronounced changes in that portion of the ECG waveform occurring during acute myocardial ischemia.

To assess the degree of agreement between each of the automated methods and the manual annotations, the Bland-Altman approach was used to estimate the mean difference and the standard deviation of differences among all beat annotations (six annotations per beat), across all subjects. The mean difference and the limits of agreement (defined as twice the standard deviation of differences) were estimated at baseline as 8.65±2.37 msec, 50.61±10.26 msec, 27.10±9.49 msec, 38.50±8.38 msec, and 48.08±9.71 msec and following coronary artery occlusion as 9.45±5.55 msec, 46.40±12.71 msec, 27.30±8.48 msec, 38.47±11.31 msec and 43.14±12.34 msec, for wavelet, waveform, power, absolute and noise methods, respectively. The mean differences as well as the margins of agreement for wavelet annotations were small enough and indicative that WT approach most closely identifies manually-determined ECG time points at baseline and following balloon occlusion.

Having established the wavelet transform as a robust method to accurately assess the ECG delineation of body-surface and intra-cardiac electrograms, the ability of the present approach to capture subtle electrogram changes underlying an abnormal electrophysiological substrate was examined. A hypothesis was verified that the proposed ischemic index would account for both changes in ventricular depolarization and repolarization, and would be a sensitive marker of acute ischemia especially for intra-cardiac electrograms.

To assess the intra-subject variability of the ischemic index, the baseline recording was split in two parts, and the standard deviation of the ischemic index was computed for each subject and lead, in the first and second half of the recording. The intra-subject variability was then quantified as the difference between the two standard deviations. A one sample t-test was applied to the differences evaluated for each lead across the whole set of subjects. The estimated p-values for the body surface, CS, LV and RV leads were 0.56, 0.96, 0.45 and 0.17, respectively, indicating that the ischemic index has significantly low intra-subject variability and presented high stability during a baseline recording, demonstrating a reliable reference for the evaluation of ischemia-induced changes.

The inter-subject variability was further evaluated by comparing the difference between the aforementioned two standard deviations with the standard deviation of the overall variability across all subjects. A one sample t-test was used to compare the intra-subject variability to the inter-subject variability of the whole population for each of the body surface and intra-cardiac leads. The p-values for the body surface, CS, LV and RV leads were computed as 0.93, 0.95, 0.46 and 0.16, respectively. These results indicated that, across all leads, there was not a statistically significant difference of the ischemic index between intra-subject variability and the standard deviation of the whole baseline across subjects. Therefore, the intra- and inter-subject variability of the ischemic index was small, making it a reliable index for the quantification of post-myocardial ischemia changes across different subjects.

Temporal changes of the ischemic index measured at the last minute of baseline prior to balloon inflation, and following coronary occlusion, were computed for the body surface and unipolar intra-cardiac leads at different time bins with a 30 second resolution for the first 5 minutes post-occlusion and a 1 minute resolution afterwards. Far-field bipolar signals obtained from leads in the RV and CS were also created.

FIG. 5A-5E shows dynamic changes of ischemic index (n=17) at baseline and following MI in body surface (FIG. 5A), unipolar intra-cardiac CS (FIG. 5B), LV (FIG. 5C), RV (FIG. 5D) and triangular RV-CS (FIG. 5E) leads. For each time-bin, the distribution of ischemic index was averaged over all study subjects. The time bin width was 1 minute for baseline, 30 sec for the first 5 minutes following balloon occlusion, and 1 minute for 5-18 minutes post-occlusion. Data are presented as median (horizontal solid line), 75-25% percentiles (box) and 90-10% percentiles (error bars). The limits of the distribution of ischemic index at baseline are shown with a gray box during the time course of myocardial ischemia to provide a visual means of comparing the one directional significance at each time point. All ischemic index distributions that were statistically greater than the baseline ischemic index distributions are indicated by an "*" (all p<0.0022).

It was observed that the ischemic index increased after the onset of ischemia, and that the ischemia-induced changes were detectable on unipolar and bipolar intra-cardiac leads as well as on body surface leads; however, the timing of the ischemia-induced changes was different across body surface and intra-cardiac leads. A statistical comparison of the distribution of ischemic index at each time bin during occlusion to that at baseline revealed that the body surface leads had the largest duration to detection, as the earliest significant change was identified after 6 minutes (P<0.0022 at all statistically significant time points). For intra-cardiac leads, the timing for the occurrence of significant changes varied with lead type, ranging from 30 sec to 90 sec after initiation of coronary occlusion (P<0.0002 for CS, P<0.0016 for LV, P<0.0020 for RV, P<0.0011 for RV-CS, at all statistically significant time points). In particular, it was found that the triangular RV-CS lead configuration offered the smallest duration to detection (30 sec) and a markedly high statistical discrimination (P<0.0011) for the early detection of the onset of acute ischemia after myocardial infarction, partly due to the broader 3-dimensional view of the myocardium and a wider solid angle to the heart when compared to unipolar leads from intra-cardiac catheters.

In summary, these results support the hypothesis that the ischemia-induced morphologic changes are most prominently seen in intra-cardiac leads. Of note, it was observed that the ischemic index remained stable and significantly elevated during coronary balloon occlusion.

To examine the time to ischemia detection using body surface and intra-cardiac signals and to investigate whether ischemia detection using intra-cardiac leads improves the probability of ischemia detection compared to body surface electrograms alone, for each time bin, the conditional probabilities of a significant change (from baseline to post-occlusion) in the ischemic index were estimated for body surface, given a significant change in the ischemic index measured from an intra-cardiac lead (n=17).

In FIG. 6A (left axis), the probability that the change in ischemic index from baseline to post-occlusion detected on a body surface lead is significant given that the change in ischemic index following balloon inflation is significantly higher in an intra-cardiac lead, is plotted for each of the CS, LV, RV, and triangular RV-CS lead configurations (quantified across all time bins). The probability (across subjects) that the change measured from a body surface lead is significant was 0.81±0.27 when CS lead showed a significant change in the ischemic index, 0.80±0.28 when LV lead showed a significant change, 0.80±0.27 when RV lead showed a significant change, and 0.80±0.27 when a lead from a triangular RV-CS configuration showed a significant increase in the ischemic index from baseline to post-occlusion.

To explore the probability of ischemia detection using intra-cardiac signals, in FIG. 6A (right axis), the probability that the change in ischemic index from baseline to post-occlusion detected on an intra-cardiac lead configuration is significant given that the change in ischemic index measured from the body surface is significantly higher in post-occlusion than baseline, is plotted for each of the CS, LV, RV, and triangular RV-CS lead configurations (quantified across all time bins). When the change of the ischemic index from baseline to post-occlusion in a body surface lead was significant, the probability that an intra-cardiac lead showed a significant change in the ischemic index was 0.95±0.07 for CS, 0.90±0.17 for LV, 0.96±0.08 for RV and 0.88±0.12 for the triangular RV-CS configuration.

Compared to the detection probabilities of body surface leads, an average improvement of 14%, 10%, 16%, and 8% was observed in the detection probabilities for CS, LV, RV and RV-CS, respectively. The results demonstrated that for all intra-cardiac leads, the probability of observing a significant change of the ischemic index in an intra-cardiac lead given a significant change in a body surface lead was always higher than the probability of observing a significant change in a body surface lead given a significant change in an intra-cardiac lead (P<0.0381). This suggested that intra-cardiac leads had higher likelihood for detecting acute ischemia. It was found that the probability of observing a significant change in RV-CS given a significant change in a body surface lead was significantly higher than the probability of observing a significant change in RV (P<0.0158). No statistical difference was found between any other two leads.

To examine which intra-cardiac lead combination has a higher probability of detecting ischemia-induced changes, in FIG. 6B, the probability of observing a significant change in an intra-cardiac lead configuration, given that a significant change has been observed in at least 1 intra-cardiac lead, is plotted for each of the CS, LV, RV, and triangular RV-CS lead configurations. It was observed that the average probability that a triangular RV-CS lead is positive was 0.96, which was greater than any other intra-cardiac lead configuration. Of note, the RV-CS probability was significantly larger than the RV configuration (P<0.0415). No statistical difference was found between any other two leads.

Finally, to assess the time-dependent likelihood of each lead to detect ischemia-induced changes, in FIG. 6C, the conditional probability (as a function of time, averaged over subjects) of observing an increase in the ischemic index exceeding 3 standard deviation from each subject's ischemic index at baseline given that a shift beyond 3 standard deviation has been observed in any lead, is plotted for each of the body-surface, CS, LV, RV, and RV-CS lead configurations. The data are presented as sigmoidal fit with the Boltzmann equation $(y=A_2+(A_1-A_2)/(1+\exp((x-x_0)/dx))$, where $A_1$ and $A_2$ represent the minimum and maximum probability, respectively; $x_0$ represents the time to half maximum probability; and $dx$ represents the slope of the exponential function). In order to fit the model only to the post-occlusion data, a constrained nonlinear optimization subject to $x_0-5dx>0$ was implemented to force the sigmoid rise to begin after the start of occlusion.

Using this method, transition times of 398, 38, 25, 2, and 6 sec, and a maximum probability of 0.75, 0.96, 0.83, 0.86, and 0.95 for body surface, CS, LV, RV and RV-CS, respectively, were obtained. The RV-CS lead configuration system was observed to provide the most accurate and rapid (combined) detection of ischemia-induced changes compared to baseline than any other lead system.

Figure 7:
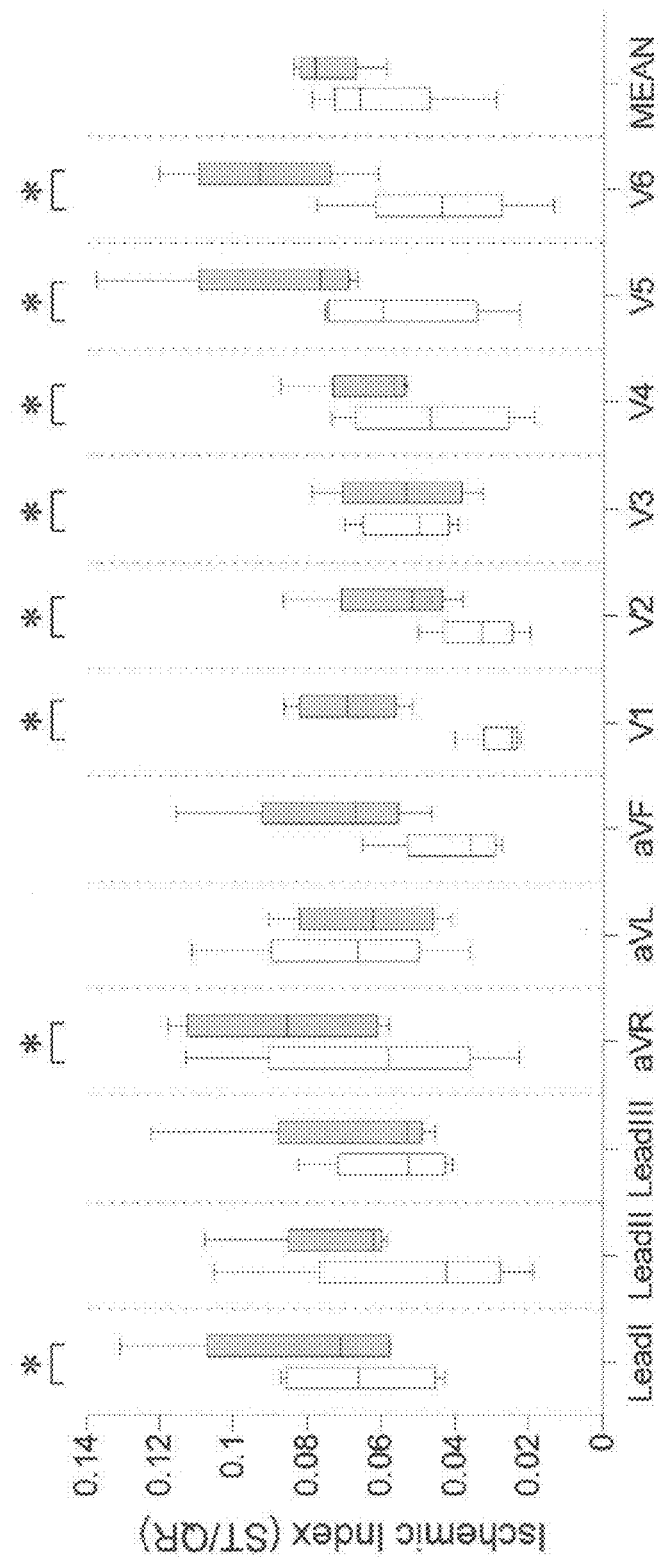
FIG. 7 is a graphical illustration showing the ischemic index computed from 24-hour Holder ECG recordings at baseline and immediately after myocardial ischemia.

A 24-hr Holter monitor was used to acquire 12 lead ECG signals (n=4) to estimate the ischemic index at baseline and following myocardial ischemia. For each subject, the median ischemic index was obtained every 1 hour during baseline and post-myocardial ischemia recordings. FIG. 7 shows the overall distribution of ischemic index at baseline and during the 24-hr following myocardial ischemia. Using the mixed model linear regression to assess the temporal changes of ischemic index from baseline to the 24-hr phase post myocardial ischemia, a statistically significant increase in Lead I, aVR and all precordial leads (P<0.0388), indicated in FIG. 7 by a "*". A marginally significant increase was observed in aVL (P<0.0523) and aVF (P<0.0607) leads. No statistically significant change from baseline to 24-hr recording post myocardial ischemia was observed in other leads.

To expand the prognostic value of the ischemic index beyond short term prediction of acute myocardial ischemia, the prediction of ventricular tachycardial events was also assessed. Specifically, the ischemic index was computed before a ventricular tachycardial event (n=9) during the acute phase of myocardial ischemia. In FIG. 8A-8E the dynamic changes of ischemic index up to 12 minutes preceding ventricular tachyarrhythmic events (n=9) in body surface (FIG. 8A), unipolar intra-cardiac CS (FIG. 8B), LV (FIG. 8C), RV (FIG. 8D) and triangular RV-CS (FIG. 8E) leads, is presented.

For the body surface leads, the ischemic index presented a significant surge (compared to a baseline before occlusion) 2 minutes prior to the event (P<0.0464) and remained marginally significant immediately before the event (P<0.0927). Compared to baseline, the intra-cardiac ischemic index before the onset of a ventricular tachycardia' event was found to remain significantly higher during the last 2 minutes in CS (P<0.0022), the last 6 minutes in LV (P<0.0464), the last minute in RV (P<0.0360), and the last 2 minutes in RV-CS (P<0.0055). Of note, the earliest significant surge in the ischemic index was observed 12 minutes before the onset of ventricular tachycardia events in RVCS leads.

Figure 9:
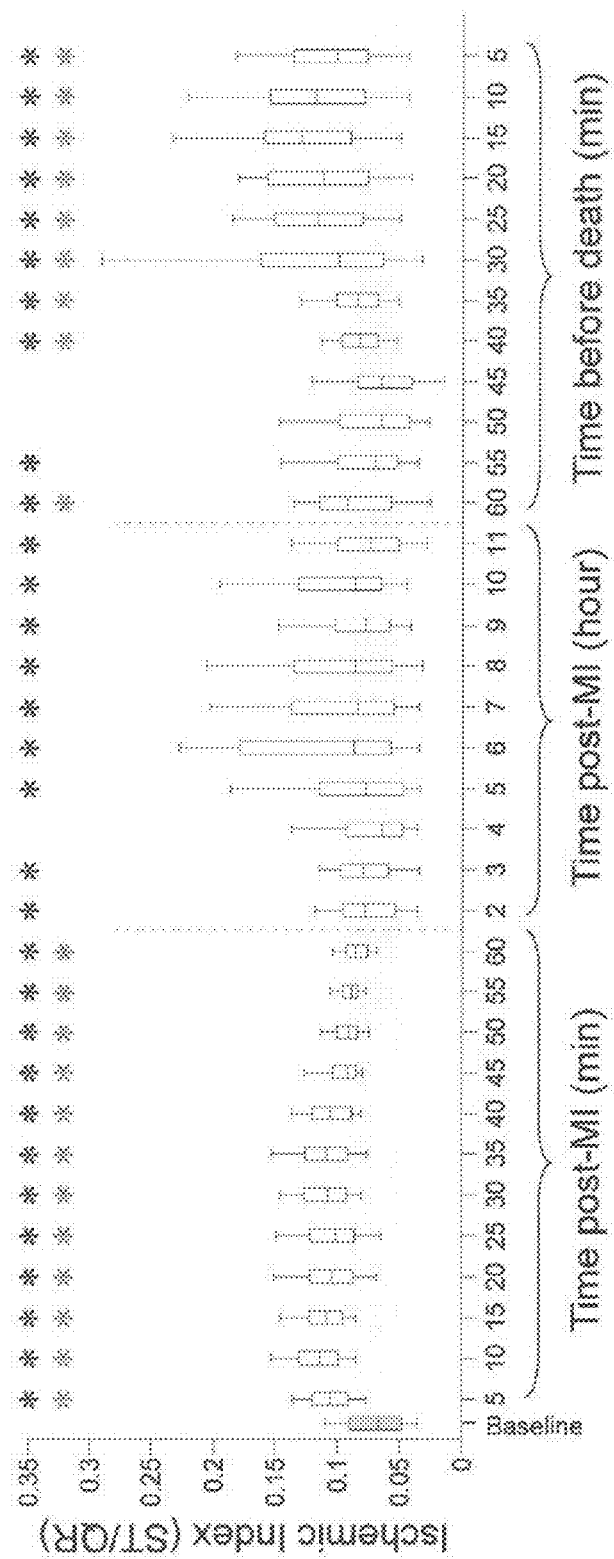
FIG. 9 is a graphical illustration showing temporal changes of the ischemic index following myocardial ischemia, from baseline until sudden cardiac death ("SCD").

The prognostic role of the ischemic index was also evaluated in a subject that experienced sudden cardiac death ("SCD") during the first 24-hr post myocardial ischemia. Shown in FIG. 9 are the dynamic changes of the ischemic index during baseline (24-hr Holter recording before myocardial ischemia induction), and the 13-hr phase post myocardial ischemia until SCD. The results obtained during the acute phase of myocardial ischemia showed a sustained elevation of the ischemic index that remained significantly higher than baseline for 3 hours post-myocardial ischemia (P<0.0001) and remained significantly higher during the $2^{nd}$ to $11^{th}$ hrs follow-up (P<0.0001). In addition, the ischemic index showed a significant increase compared to baseline 40 minutes before death (P<0.0001). Of note, a comparison between the ischemic index during the $2^{nd}$ to $11^{th}$ hrs post-myocardial ischemia showed a significant increase 40 minutes prior to the event (P<0.0001).

Taken together, the above findings suggested that an increase in the ischemic index may play an important prognostic role in the early detection of ventricular tachycardia events. In addition, monitoring the intra-cardiac ischemic index from the triangular RV-CS leads may provide an earlier prediction of the impending arrhythmia onset.

In summary, early identification of cardiac conditions allows for prompt intervention that may help improve clinical outcomes. Hence, the present disclosure provides systems and methods for determining and controlling cardiac conditions using electrocardiogram ("ECG") measurements. The provided system and method implement a novel approach that relies on accurate delineation of waveform and characteristics associated with acquired ECG signals. In addition, an ischemic index is introduced to quantify beat-to-beat changes observed in both ventricular depolarization and repolarization periods of a cardiac cycle, facilitating determination of a cardiac condition of the subject, such as acute or long-term myocardial ischemia. Such approach may help detect dynamic unstable or worsening ischemia and provide a trigger for appropriate ischemic treatment. Furthermore, the herein introduced ischemic index may serve as a predictor of ventricular tachycardia events.

Despite the dynamic beat-to-beat and subject-to-subject variability of ECG morphology, data shown herein indicate that the introduced ischemic index presents high stability as well as very low intra- and inter-subject variability under non-ischemic conditions. In addition, estimation of the ischemic index using intra-cardiac signals has been shown to provide a highly efficient and accurate means of detecting the onset of an acute or the progression of an ongoing ischemic episode, with intra-cardiac leads exhibiting a greater ability of detecting myocardial ischemia-induced changes compared to body surface leads.

The above-described system and method implementing computations of an ischemic index may provide a clinically feasible means for detecting the early onset of acute ischemia, for example associated with thrombotic occlusion, and provide an early trigger of appropriate medical therapy. In particular, the system and method of the present disclosure may be particularly beneficial for patients at high risk for recurrent coronary syndromes. Beyond the setting of acute coronary syndromes, data presented herein also suggest that detection of ischemia, and particularly using intra-cardiac leads, may play an important role in the diagnosis and treatment of patients with "silent" ischemia, which is associated with adverse clinical outcomes and is likely underdiagnosed due to the lack of effective screening tools. With a real-time shift from hours to minutes from the onset of coronary occlusion, patients who otherwise experience adverse clinical courses or lethal dysrhythmias may receive pre-symptomatic warnings in a time frame of life-saving proportion using the system and method provided by the present disclosure.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for determining a cardiac condition of a subject, the monitoring system comprising:
   one or more electrodes configured to sense a cardiac activity of a subject; and
   a processor configured to:
   i. receive ECG signals acquired using the one or more electrodes;
   ii. analyze the ECG signals to delineate cardiac waveforms on a beat-to-beat basis;
   iii. identify, in the delineated cardiac waveforms, characteristic points associated with different phases of cardiac activity;
   iv. for each delineated cardiac waveform, compute an ischemic index using a combination of ECG signals corresponding to a ventricular depolarization period and a ventricular repolarization period, wherein the ventricular depolarization period and the ventricular repolarization period are defined by the characteristic points identified in step iii) and at least one ischemic index is computed by taking a ratio between an ST height and an amplitude of a QR segment;
   v. determine a cardiac condition of the subject using at least one ischemic index computed;
   vi. generate a report indicative of the cardiac condition of the subject.

2. The system of claim 1, wherein the one or more electrodes includes at least one of an intra-cardiac electrode or a body surface electrode.

3. The system of claim 2, wherein the at least one intra-cardiac electrode includes at least one of a right ventricle electrode, or a left ventricle electrode, or a coronary sinus electrode, or a combination of electrodes therefrom.

4. The system of claim 1, wherein processor is further configured to detect at least one of an R-wave peak in the received ECG signals.

5. The system of claim 1, wherein the processor is further configured to apply a template-matching alignment algorithm to obtain the delineated cardiac waveforms.

6. The system of claim 1, wherein the processor is further configured to perform a wavelet transform technique, using the received ECG signals, to identify the characteristic points at step iii).

7. The system of claim 6, wherein the processor is further configured to estimate at least one dyadic wavelet transform for scales wherein a substantial energy of the delineated cardiac waveform lies.

8. The system of claim 1, wherein the processor is further configured to compute the ischemic index by taking an absolute value or a real value of a ratio between the ST height and the amplitude of the QR segment.

9. The system of claim 1, wherein the processor is further configured to estimate the ST height by computing a mean or a median of ECG signals that are between an offset of a QRS complex and an onset of a T-wave and have values in excess of an isoelectric baseline associated with a delineated cardiac waveform.

10. The system of claim 9, wherein the processor is further configured to obtain the isoelectric baseline using the ECG signals associated with a PR segment of the delineated cardiac waveform.

11. The system of claim 9, wherein the processor is further configured to obtain the isoelectric baseline using the ECG signals associated with a TP segment of the delineated cardiac waveform.

12. The system of claim 1, wherein the processor is further configured to determine the cardiac condition of the subject by comparing the at least one ischemic index computed at step iv) with a baseline value.

13. The system of claim 1, the system further comprising a therapy module in communication with the processor, wherein the therapy module is configured to provide a treatment to the subject as a result of the determined cardiac condition.

14. The system of claim 13, wherein the treatment includes administration of an electrical stimulation.

15. The system of claim 13, wherein the treatment includes administration of at least one pharmaceutical agent.

16. The system of claim 1, wherein the processor is further configured to identify a myocardial ischemia or a ventricular tachycardia using the at least one ischemic index computed.

17. A method for determining a cardiac condition of a subject, the method comprising:
   a. acquiring ECG signals using one or more electrodes configured to sense a cardiac activity of a subject;
   b. analyzing the ECG signals to delineate cardiac waveforms on a beat-to-beat basis;
   c. identifying, in the delineated cardiac waveforms, characteristic points associated with different phases of cardiac activity;
   d. for each delineated cardiac waveform, computing an ischemic index using a combination of ECG signals corresponding to a ventricular depolarization period and a ventricular repolarization period, wherein the ventricular depolarization period and the ventricular repolarization period are defined by the characteristic points identified in step c), and at least one ischemic index is computed by taking a ratio between an ST height and an amplitude of a QR segment; and
   e. determining a cardiac condition of the subject using at least one ischemic index computed.

18. The method of claim 17, the method further comprising acquiring the ECG signals using at least one of an intra-cardiac electrode or a body surface electrode.

19. The method of claim 18, the method further comprising acquiring the ECG signals using at least one of a right ventricle electrode, or a left ventricle electrode, or a coronary sinus electrode, or a combination of electrodes therefrom.

20. The method of claim 17, the method further comprising detecting at least one of an R-wave peak in the ECG signals acquired.

21. The method of claim 17, the method further comprising applying a template-matching alignment algorithm to obtain the delineated cardiac waveforms.

22. The method of claim 17, the method further comprising performing a wavelet transform technique, using the received ECG signals, to identify the characteristic points at step c).

23. The method of claim 22, the method further comprising estimating at least one dyadic wavelet transform for scales wherein a substantial energy of the delineated cardiac waveform lies.

24. The method of claim 17, the method further comprising taking an absolute value or a real value of the ratio.

25. The method of claim 17, the method further comprising estimating the ST height by computing a mean or a median of ECG signals that are between an offset of a QRS complex and an onset of a T-wave and have values in excess of an isoelectric baseline associated with a delineated cardiac waveform.

26. The method of claim 17, the method further comprising determining the cardiac condition of the subject by comparing a computed ischemic index at step d) with a baseline value.

27. The method of claim 17, the method further comprising identifying a myocardial ischemia or a ventricular tachycardia using the at least one ischemic index computed.

\* \* \* \* \*

UNITED STATES PATENT AND TRADEMARK OFFICE
CERTIFICATE OF CORRECTION

PATENT NO. : 9,949,659 B2
APPLICATION NO. : 14/671395
DATED : April 24, 2018
INVENTOR(S) : Antonis Armoundas Page 1 of 1

It is certified that error appears in the above-identified patent and that said Letters Patent is hereby corrected as shown below:

In the Specification

Column 17, Line 66, "tachycardia'" should be -- tachycardial --.

Signed and Sealed this
Fifth Day of June, 2018

Andrei Iancu
*Director of the United States Patent and Trademark Office*